US011633095B2

(12) United States Patent
Jacobson et al.

(10) Patent No.: US 11,633,095 B2
(45) Date of Patent: Apr. 25, 2023

(54) SYSTEM FOR ULTRA-WIDE FIELD IMAGING OF THE POSTERIOR SEGMENT

(71) Applicant: Optos Plc, Dunfermline (GB)

(72) Inventors: Benjamin A. Jacobson, Santa Barbara, CA (US); Clark Pentico, Simi Valley, CA (US); Andre E. Adams, Tiburon, CA (US); Brendan Hamel-Bissell, San Francisco, CA (US); Tushar M. Ranchod, Berkeley, CA (US)

(73) Assignee: OPTOS PLC, Dunfermline (GB)

( * ) Notice: Subject to any disclaimer, the term of this patent is extended or adjusted under 35 U.S.C. 154(b) by 555 days.

(21) Appl. No.: 16/698,024

(22) Filed: Nov. 27, 2019

(65) Prior Publication Data

US 2020/0163544 A1 May 28, 2020

Related U.S. Application Data

(60) Provisional application No. 62/772,496, filed on Nov. 28, 2018.

(51) Int. Cl.
*A61B 3/00* (2006.01)
*A61B 3/12* (2006.01)
*A61B 3/14* (2006.01)
*A61B 3/125* (2006.01)

(52) U.S. Cl.
CPC .......... *A61B 3/0008* (2013.01); *A61B 3/0058* (2013.01); *A61B 3/125* (2013.01); *A61B 3/145* (2013.01); *A61B 2562/028* (2013.01)

(58) Field of Classification Search
CPC ..... A61B 3/0008; A61B 3/1208; A61B 3/125; A61B 3/0058; A61B 3/0075; A61B 3/10; A61B 3/12; A61B 3/1225; A61B 3/14; A61B 3/145

USPC .................................................. 359/618, 630
See application file for complete search history.

(56) References Cited

U.S. PATENT DOCUMENTS

| | | | |
|---|---|---|---|
| 2004/0170304 A1 | 9/2004 | Haven et al. | |
| 2005/0018309 A1* | 1/2005 | McGuire, Jr. ...... | G02B 27/0081 359/630 |
| 2005/0249377 A1 | 11/2005 | Fouquet et al. | |
| 2013/0128224 A1* | 5/2013 | Wall ..................... | A61B 3/0008 351/221 |

(Continued)

FOREIGN PATENT DOCUMENTS

WO    2019241000 A1    12/2019

OTHER PUBLICATIONS

PCT International Search Report and Written Opinion issued in corresponding application PCT/US2019/063600, dated Jan. 24, 2020.

(Continued)

*Primary Examiner* — Dawayne Pinkney
(74) *Attorney, Agent, or Firm* — DeLucia, Mlynar & Associates LLP

(57) ABSTRACT

A device for illuminating a posterior segment of an eye may include multiple channels. Each of the channels may include multiple illumination paths such as a first region illumination path, and a second region illumination path. The first region illumination path and the second region illumination path may be illuminated at different times such that a first region and a second region may be imaged without interference from a non-illuminated illumination path.

23 Claims, 26 Drawing Sheets

(56) References Cited

U.S. PATENT DOCUMENTS

| | | |
|---|---|---|
| 2013/0271728 A1 | 10/2013 | Ranchod |
| 2013/0271729 A1* | 10/2013 | Ranchod ................ A61B 3/117 351/246 |
| 2016/0183788 A1* | 6/2016 | Abramoff ............ A61B 3/0008 351/208 |
| 2016/0249806 A1* | 9/2016 | Yates .................... A61B 3/125 351/207 |
| 2018/0110651 A1 | 4/2018 | Gomzalez |
| 2019/0159673 A1 | 5/2019 | Yates et al. |

OTHER PUBLICATIONS

International Preliminary Report on Patentability dated May 25, 2021 in International Application No. PCT/US2019/063600.
Supplementary European Search Report dated Nov. 2, 2022 in European Patent Application No. 19 89 1411 (10 sheets).

* cited by examiner

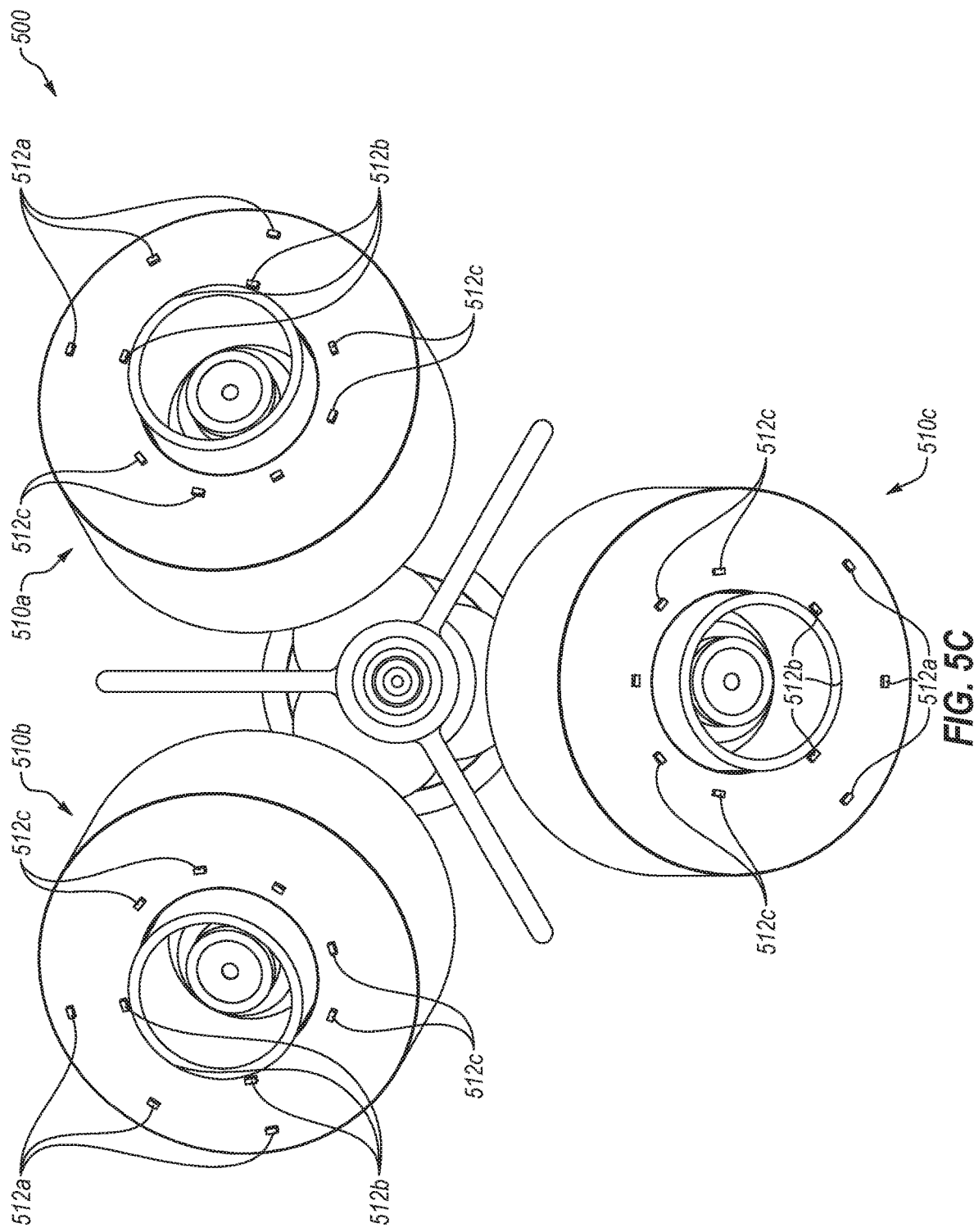

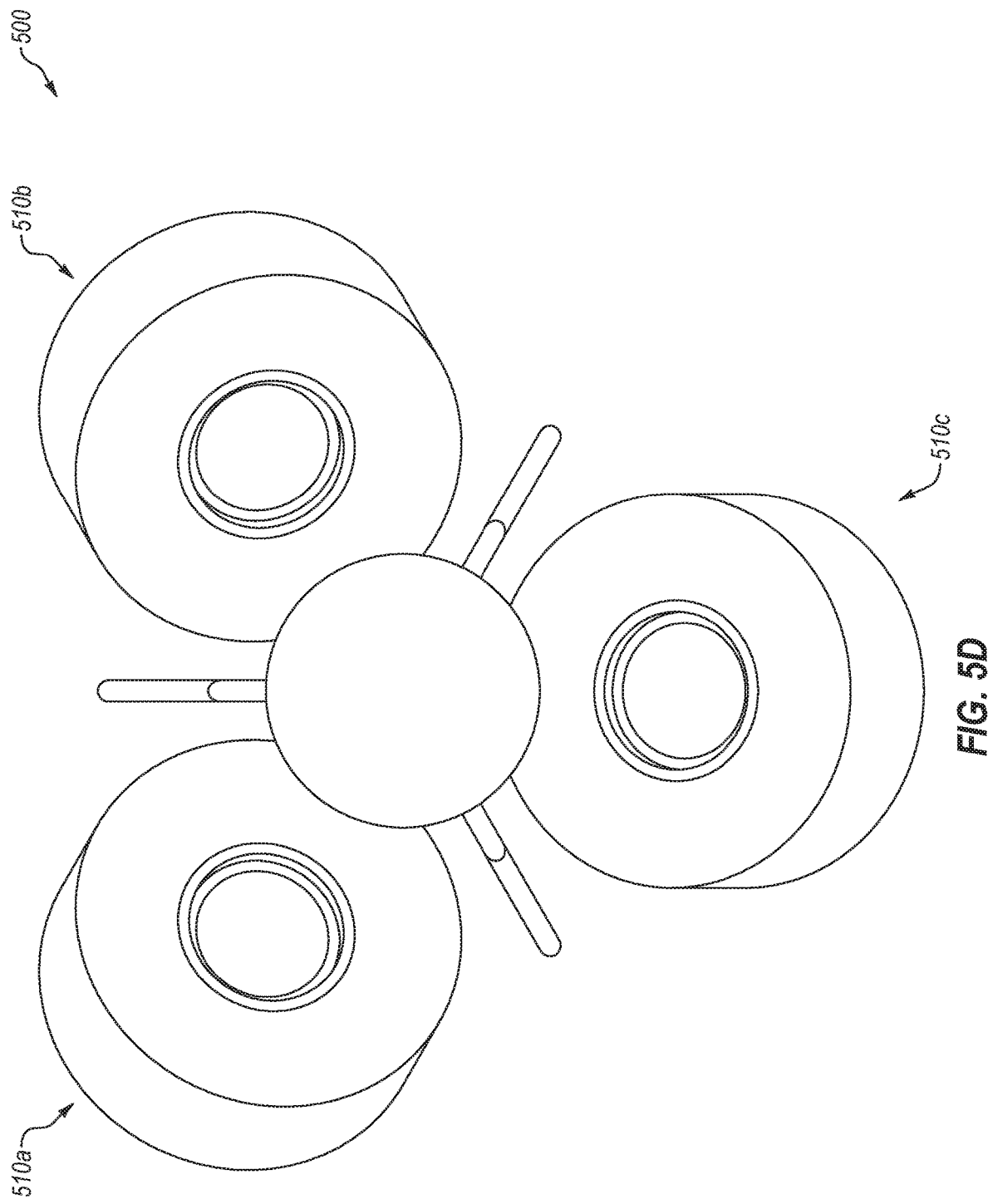

SYSTEM FOR ULTRA-WIDE FIELD IMAGING OF THE POSTERIOR SEGMENT

CROSS-REFERENCE TO RELATED APPLICATIONS

This application claims the benefit of U.S. Patent Application Ser. No. 62/772,496, filed on Nov. 28, 2018; the disclosure of which is incorporated herein by reference in its entirety.

FIELD

The present disclosure relates generally to a system for ultra-wide field imaging of the posterior segment of the eye.

BACKGROUND

Ocular imaging is commonly used both to screen for diseases and to document findings discovered during clinical examination of the eye. Specifically, documentation and analysis of the posterior segment of the eye (e.g., retinal imaging) may be relevant to comprehensive eye examinations and full evaluations of current conditions, treatment, and/or early prevention of various eye conditions and diseases.

To achieve wider field of view images, some approaches utilize a laser-scanning image illumination approach. However, such images are not true to color, and require a very large device. Another approach includes a traditional fundus camera (a low-powered microscope with an attached camera for retinal imaging) that is repeatedly repositioned to capture successive images, and numerical algorithms are used to form a composite image from each of the individual repositioned images.

The subject matter claimed herein is not limited to embodiments that solve any disadvantages or that operate only in environments such as those described above. Rather, this background is only provided to illustrate one example technology area where some embodiments described herein may be practiced.

SUMMARY

One embodiment of the present disclosure may include a device for illuminating the posterior segment of an eye, with the device including multiple channels. Each of the channels may include two or more regions of illumination such as a first region illumination path, and a second region illumination path. The first region illumination path and the second region illumination path may be illuminated at different times such that a first region and a second region may be imaged without interference from a non-illuminated illumination path.

One or more of the objects and/or advantages of the embodiments will be realized or achieved at least by the elements, features, and combinations particularly pointed out in the claims.

It is to be understood that both the foregoing general description and the following detailed description are given as examples and explanatory and are not restrictive of the present disclosure, as claimed.

BRIEF DESCRIPTION OF FIGURES

Example embodiments will be described and explained with additional specificity and detail through the use of the accompanying drawings in which:

FIGS. 5A-5D illustrate various aspects of an example illumination system;

all according to at least one embodiment described in the present disclosure.

DESCRIPTION OF EMBODIMENTS

In some embodiments of the present disclosure, distinct image channels may be used to image a wide field of view of the posterior segment of the eye using a single device. In particular, the three distinct channels are oriented about a common axis such that multiple regions of the posterior segment may be imaged without readjusting the location of the imaging device. To facilitate the wide field of view, different portions of the posterior segment may be illuminated at different times to avoid interference by the illumination beams with the imaging channel.

Figure 1B:
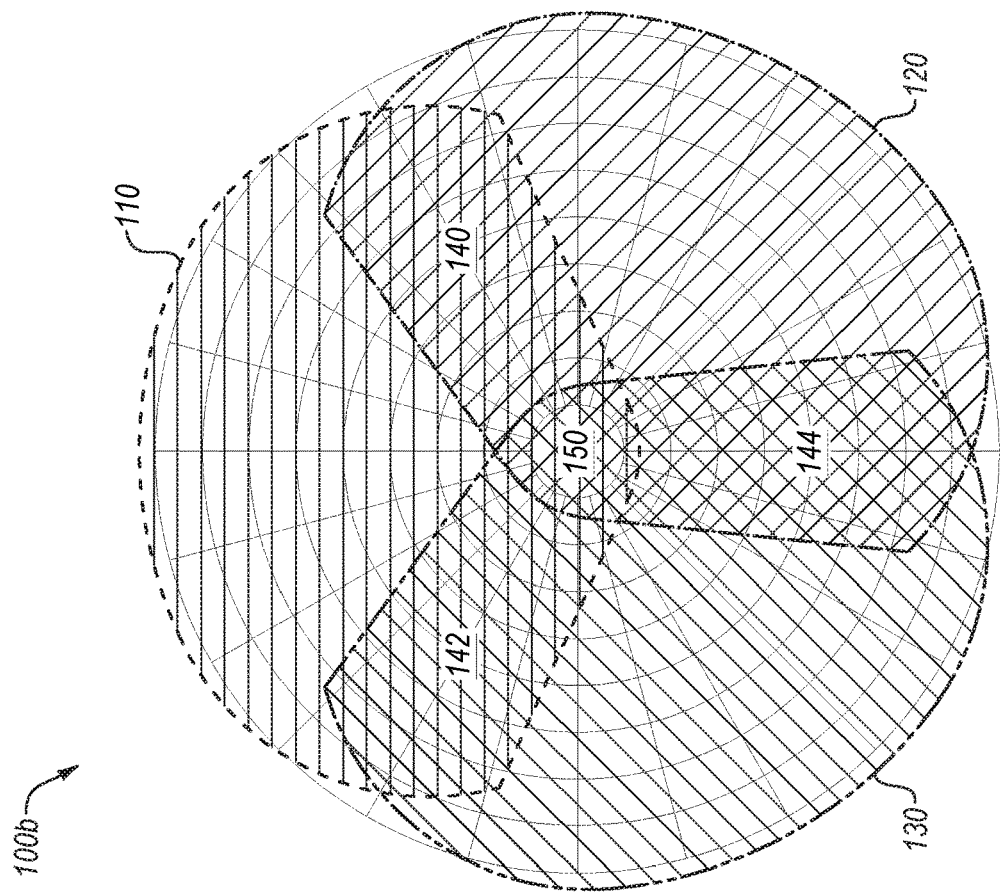
FIGS. 1A and 1B illustrate a circular shape with gridlines, representing the posterior segment of an eye.
Figure 1A:
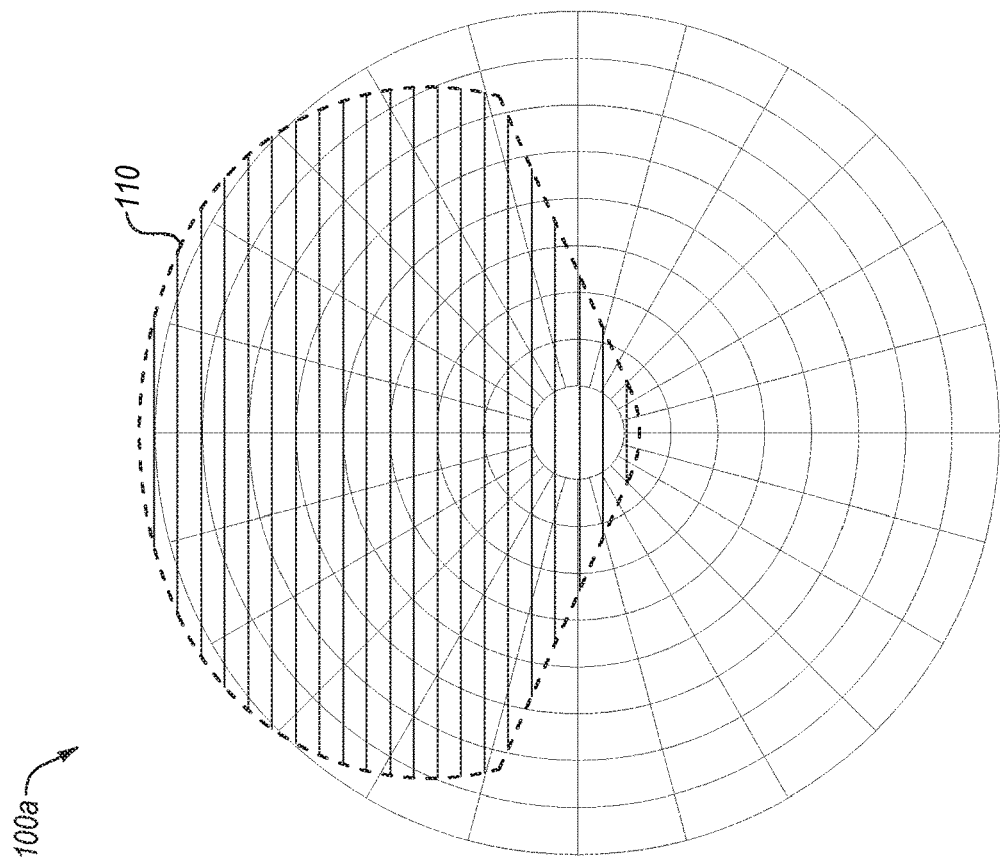

FIGS. 1A and 1B illustrate a circular shape with gridlines, representing the posterior segment 100a of the eye. Overlaid on the posterior segment 100a is a first region 110 representing a portion of the posterior segment 100a that is imaged and/or illuminated by a first imaging channel.

As illustrated in FIG. 1B, the posterior segment 100b may be covered by multiple channels. For example, the first region 110 covered by the first imaging channel is illustrated, a second region 120 covered by a second imaging channel is illustrated, and a third region 130 covered by a third imaging channel. The three regions 110, 120, and 130 include overlapping regions such that nearly the entire posterior segment is covered by the three regions 110, 120, and 130. For example, the overlapping regions 140, 142, and 144 (as illustrated by the hashmarks) illustrate regions covered by two imaging channels, and the overlapping region 150 illustrates a region covered by all three imaging channels. By using this pattern of overlap, the central region of the posterior segment is covered by all three imaging channels. Additionally, as explained below, the use and orientation of the three imaging channels permits an imaging device to image all three channels via a handheld device without reorienting the imaging device relative to the eye.

In some embodiments, each of the imaging channels include an individual imaging system with an imaging sensor, filters, etc. The imaging systems may be a smaller scale compared to typical fundus cameras. For example, the three imaging channels together may fit into a single handheld device. In these and other embodiments, the three imaging channels may be offset from each other about the center of the imaging device and may be angled to cover the corresponding region 110, 120, or 130. For example, the imaging systems may be offset from each other by one hundred and twenty degrees about the center point of the imaging device. In another embodiment, the imaging systems may be offset from the central axis of the imaging device by different or variable angles, with or without asymmetric regions of the retina imaged by each imaging system. In yet another embodiment, the imaging systems offset from the central axis may be combined with an imaging channel that is on-axis relative to the device and/or the optical axis of the eye.

Figure 2B:
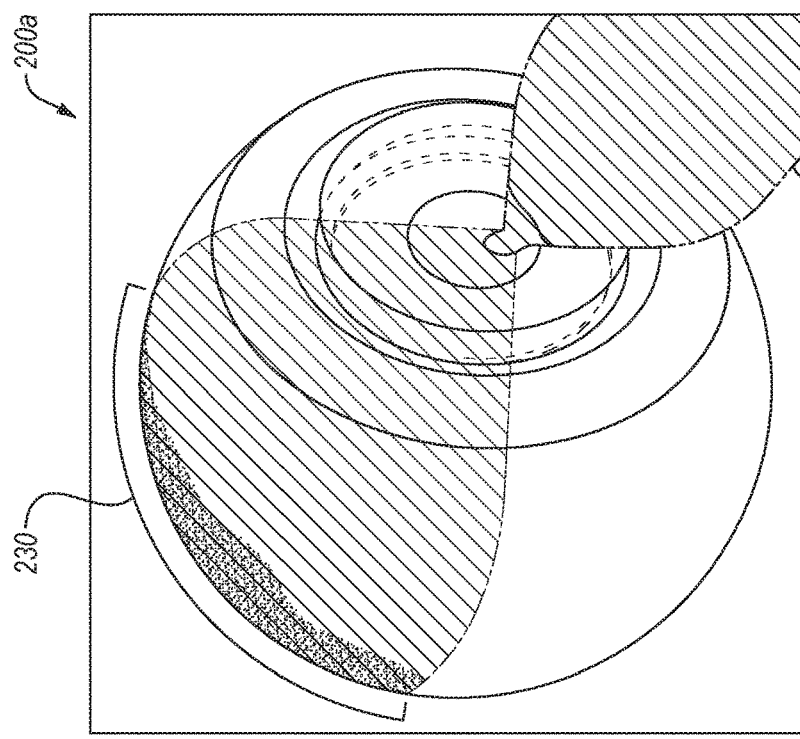
FIGS. 2A and 2B illustrate an example of a single imaging channel.
Figure 2A:
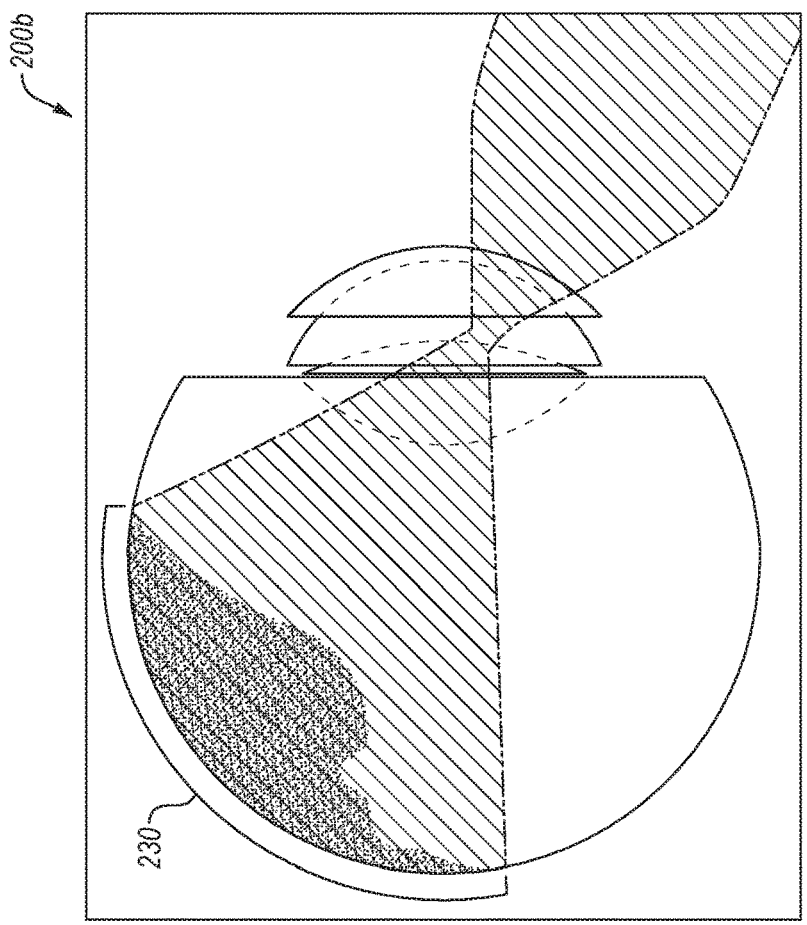
Figure 3:
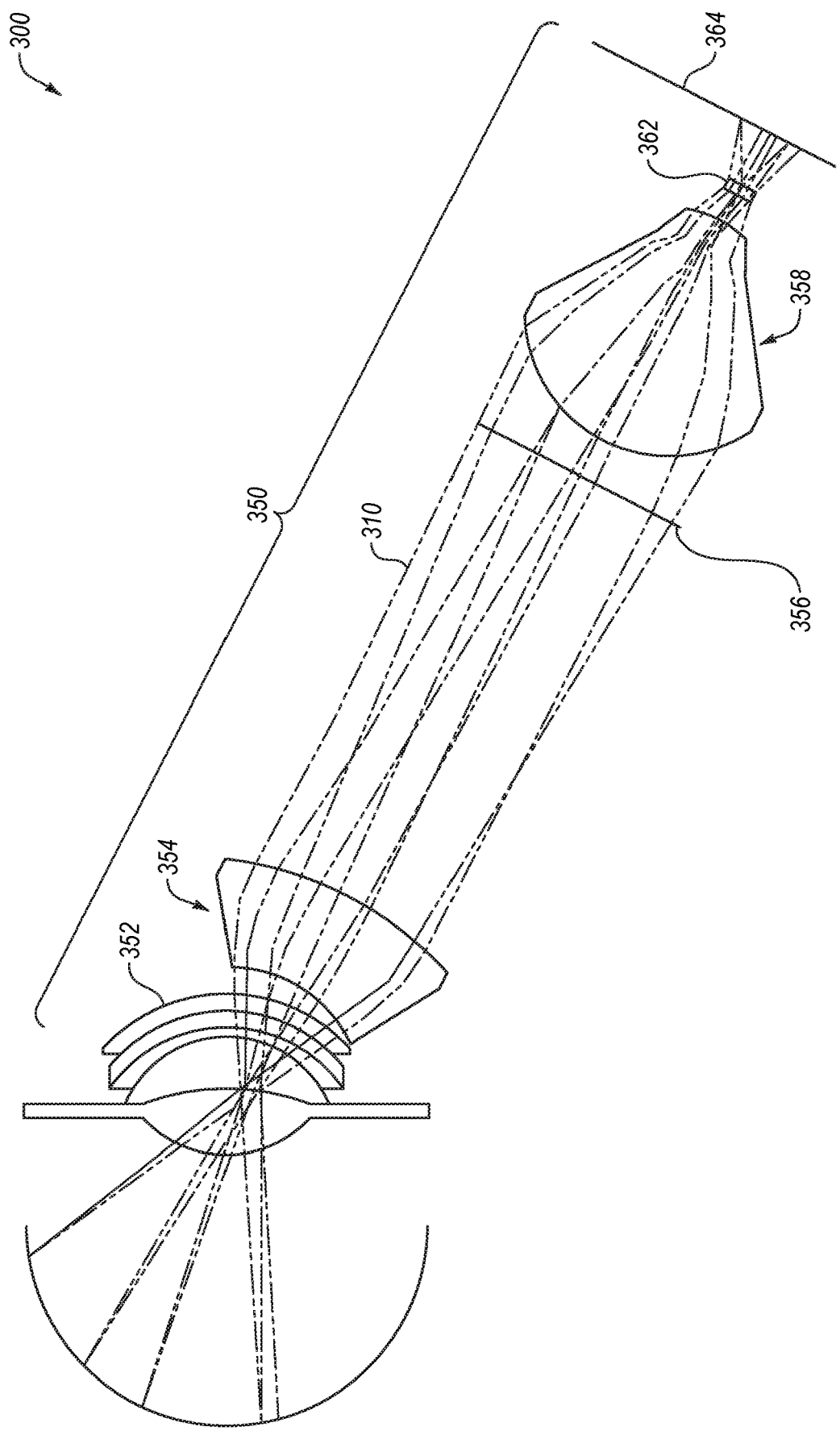
FIG. 3 illustrates another example of a single imaging channel.

FIGS. 2A and 2B and FIG. 3 illustrate a single imaging channel. FIGS. 2A and 2B illustrate systems 200a and 200b of the optical traces 210 of the imaging path for the single imaging channel. FIG. 3 illustrates various portions of the imaging system 300 of the single imaging channel, such as lenses, windows, sensors, etc.

As illustrated in FIGS. 2A and 2B, the optical traces 210 illustrate the imaging optical path as it passes through the anterior segment of the eye to image the region 230 of the posterior segment of the eye.

As illustrated in FIG. 3, the imaging system 300 illustrates the optical traces 310 of imaging of the posterior segment. As illustrated in FIG. 3, the imaging system 300 may include a single imaging channel 350. The single imaging channel 350 may include a glass window 352, one or more glass lenses 354, one or more polarizers 356, one or more relay lenses 358, one or more camera sensors 364, and a camera aperture 362. To facilitate understanding of the location and interaction of the various components of the single imaging channel 350, the optical traces 310 illustrate a path from the retina of the eye to the camera sensor 359.

As illustrated in FIG. 3, tracing from the back wall of the eye at the retina, the optical traces 310 pass through the posterior lens and pass out at the anterior lens of the eye. Where the optical traces 310 pass out of the anterior lens and into the cornea is the entrance/exit point for the imaging path to/from the inside of the eye for the imaging system 300. As the optical traces 310 pass through the cornea, they then pass through a glass window 352 of the single imaging channel 350 at an end of the single imaging channel 350 proximate the eye. The glass window 352 may be the physical interface between the imaging device and the eye, and may be shaped with a curvature that is shaped to interface with the eye (e.g., with a curvature that matches an average eye curvature). In some embodiments, the glass window 352 may be oriented and aligned with a center of the eye and may be of a size that each of the multiple imaging channels may pass through the glass window 352, rather than including a glass window for each channel. Additionally or alternatively, each of the multiple imaging channels may include their own glass window. In some embodiments, the glass window 352 may be positioned in direct contact with the cornea with or without a coupling gel or fluid, while in other embodiments the glass window 352 may be positioned some distance away from the cornea.

After passing through the glass window 352, the optical traces 310 may pass through one or more glass lenses 354, such as the glass lens 1 354a and the glass lens 2 354b. The initial glass lenses 354 may cause the optical traces 310 from the single imaging channel 350 to form at an intermediate image that may be located at about one third of the length of the imaging path for the single imaging channel 350. In some embodiments, the single imaging channel 350 may be oriented approximately twenty five degrees off of the center axis of the eye and/or the center line of the multi-channel imaging device, although any position, such as between five and forty-five degrees off of the center axis are contemplated. In these and other embodiments, the angle may be modified based on the entrance pupil position and/or the mechanical mounting of the single channels 350 within the multi-channel imaging device.

The optical traces 310 may continue on through the single imaging channel 350 to pass through a cleanup polarizer 356. The cleanup polarizer 356 may be configured to act as a polarization filter such that any light reflected back towards the camera sensor 364 from surfaces within the single imaging channel 350 from an orthogonally polarized illumination source may be filtered out while allowing the unpolarized light scattered off of the retina to pass through the cleanup polarizer 356 for imaging. In some embodiments, the polarized illumination source may be oriented using a filter or other feature. In some embodiments, the illumination source and/or the cleanup polarizer 356 may be tunable.

The optical traces 310 may continue on through the single imaging channel 350 to pass through one or more relay lenses 358 which may include individual relay lenses or any system of relay lenses. While illustrated as a single relay lens 358, any number of reflective or refractive optical elements may be included. As illustrated in FIG. 3, there is one relay system (e.g., the relay lens 358) and camera (the camera sensor 364 and/or the camera aperture 362) per objective and the relay system may be aligned to the objective. The present disclosure may be multiple cameras with relays, each oriented toward the intermediate image in a patterned or random arrangement.

As the relay lens 358 begins to focus the beams of the single imaging channel 350, the optical traces 310 may pass through the camera aperture 362 and arrive at the camera sensor 364 for capturing an image of the posterior segment of the eye. In some embodiments, the intermediate image plane may be aligned to a plane of the camera sensor 364. The camera aperture 362 may be aligned with the plane of the camera sensor 364 and may be conjugate to the system entrance pupil (e.g., the entrance pupil position illustrated in FIG. 3).

As illustrated in FIG. 3, the single imaging channel 350 is offset from the center of the eye such that multiple such single channels may be disposed within the same single imaging device.

Figure 4A:
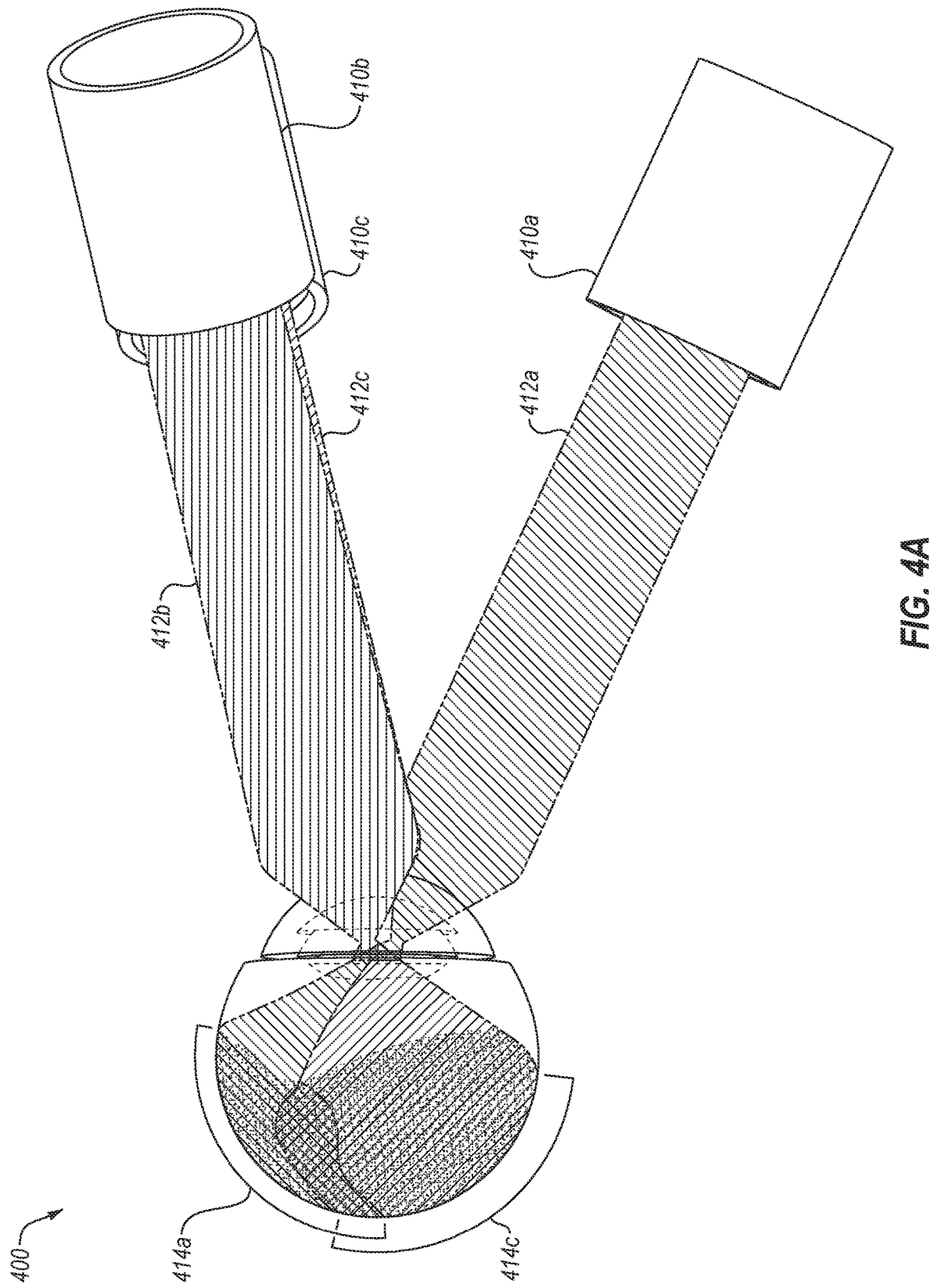
FIGS. 4A-4D illustrate an example of a multi-channel imaging system.
Figure 4B:
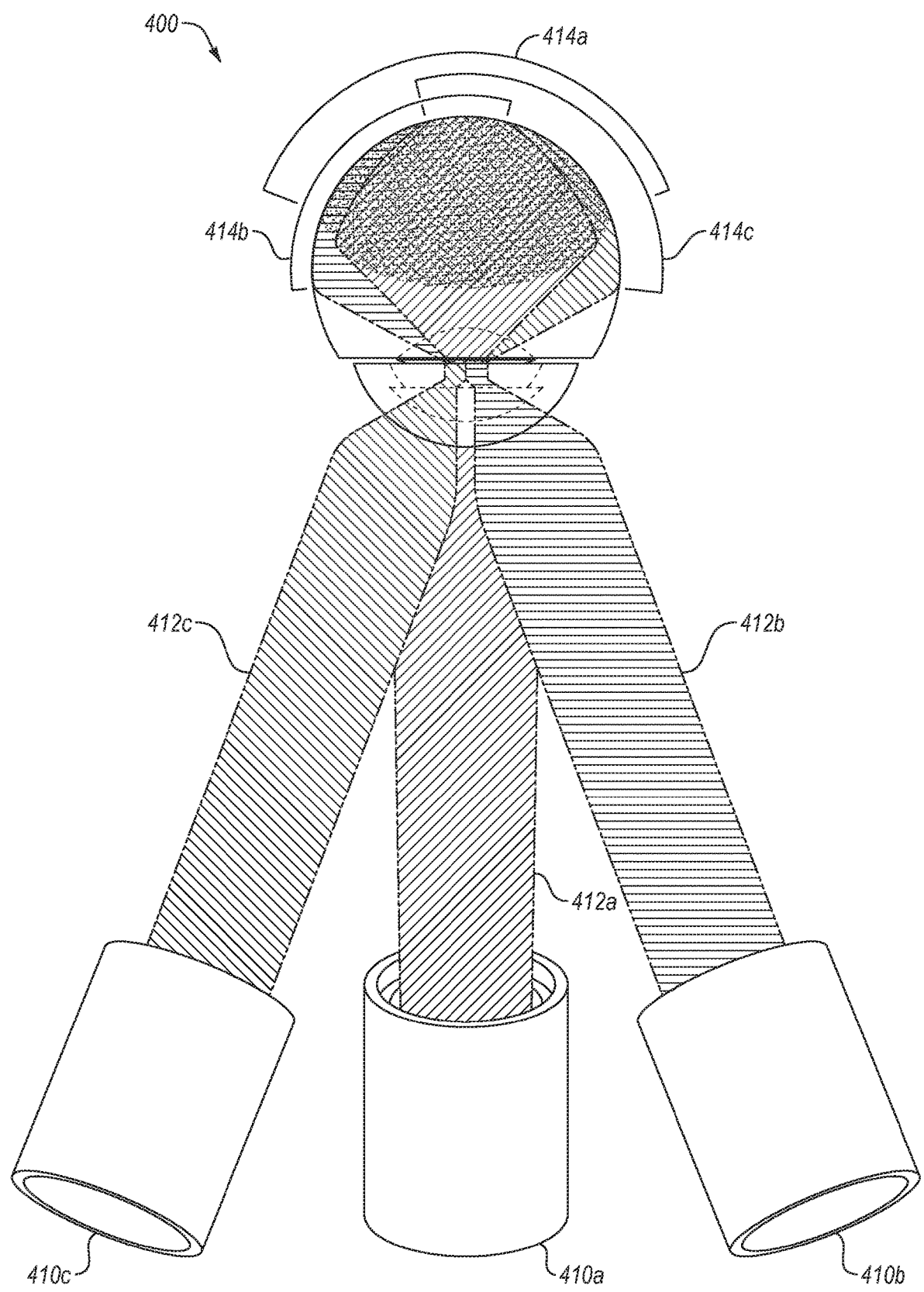
Figure 4D:
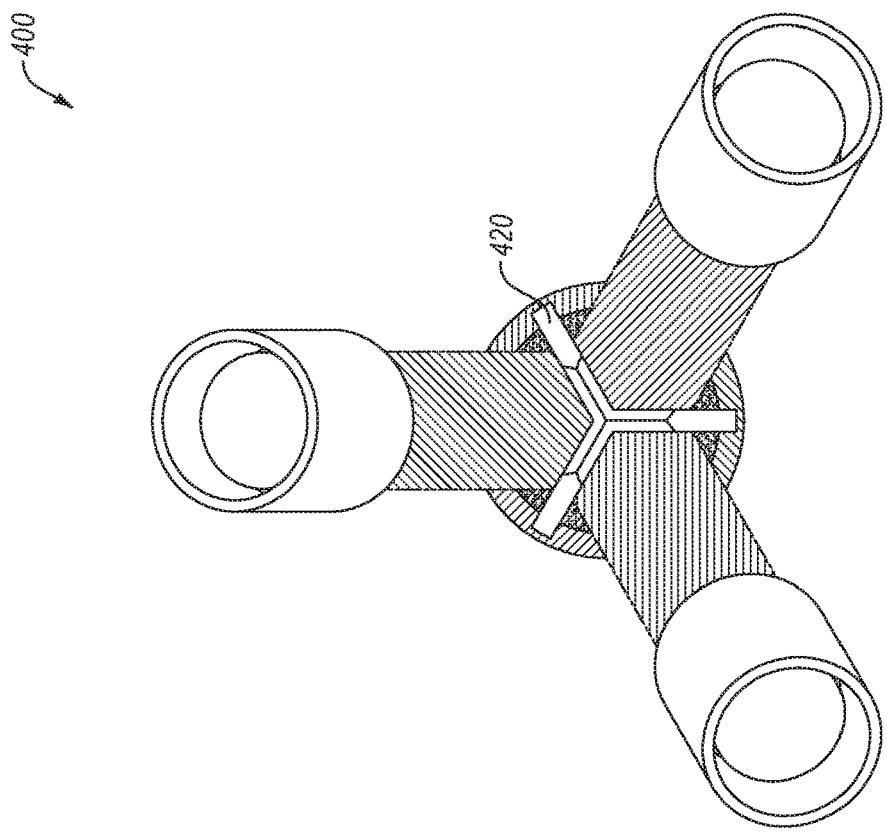
Figure 4C:
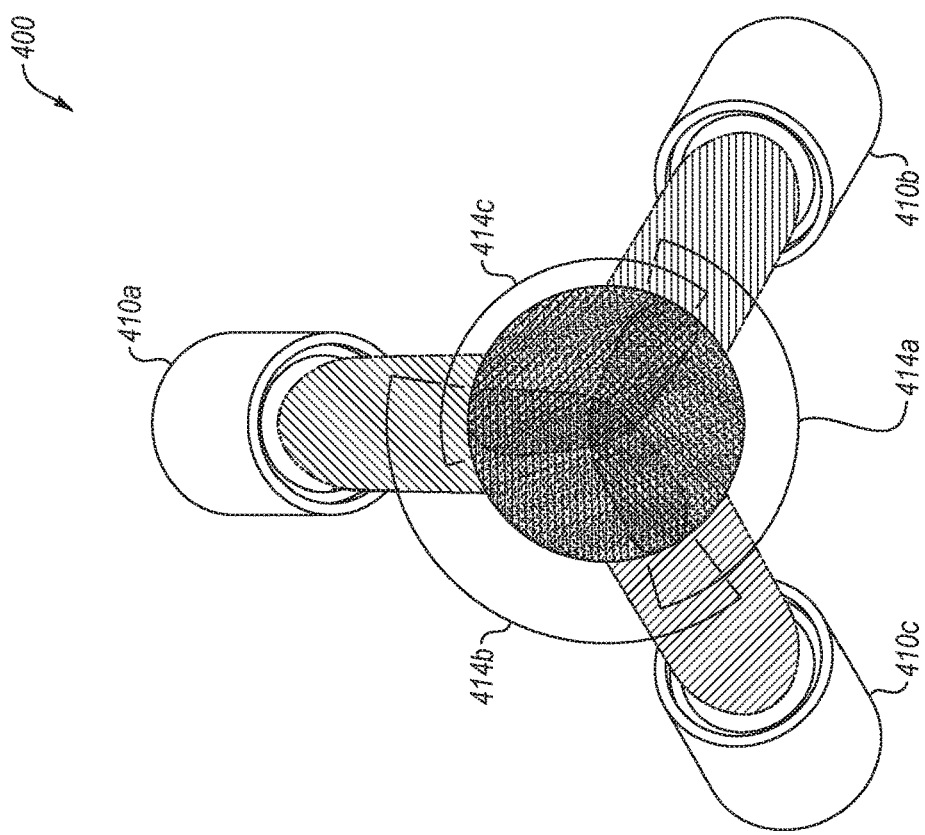

FIGS. 4A-4D illustrates a multi-channel imaging system 400. FIG. 4A illustrates a side view of the multi-channel imaging system 400, FIG. 4B illustrates a top-down view of the multi-channel imaging system 400, FIG. 4C illustrates a front view of the multi-channel imaging system 400 (e.g., from the eye looking out towards the multi-channel imaging system), and FIG. 4D illustrates a back view of the multi-channel imaging system 400.

As illustrated in FIGS. 4A-4D, the first imaging channel 410a may include the optical traces 412a to illustrate the imaging of the first region 414a, the second imaging channel 410b may include the optical traces 412b to illustrate the imaging of the second region 414b, and the third imaging channel 410c may include the optical traces 412c to illustrate the imaging of the third region 414c. While illustrated as three equally-spaced channels, any number of channels and spacing of those channels may be included. For example, two, four, five, six, or any number of channels may be used. As another example, rather than being equally distributed, the channels may be arranged in a varied or weighted arrangement, rather than equally distributed.

In some embodiments, because the three illustrated imaging channels converge on a single point, there is overlap at the apex of the three imaging channels. To address the overlap, the imaging channels may be truncated symmetrically and mounted against a symmetrical three-section wall 420. In these and other embodiments, the different sections of the three-section wall 420 may function as axial baffles to block light from crossing between the different channels. In some embodiments, the imaging channels may be truncated in an asymmetric manner and mounted against an asymmetric wall 420. In some embodiments, the wall 420 may contain within it optical illumination and/or imaging channels that are separate from those described herein. In some embodiments, if more than three channels are used the wall 420 may be a multi-sectioned wall with a same number of sections as there are channels.

In some embodiments, the glass lenses of the individual channels may be individually cut and mounted so as to be separated by the three-section wall 420. Additionally or alternatively, the glass lenses may be mounted without the three-section wall 420. In these and other embodiments, the glass lenses across the distinct channels may be molded together as a single component and/or be mounted as separate components.

In some embodiments, a single glass window may be used across all three channels. Additionally or alternatively, the present disclosure contemplates multiple windows for multiple channels, and/or no window. For example, if the imaging device does not contact the eye, a glass window may not be used. In these and other embodiments, an objective lens may contact the cornea, or a contact lens or other barrier may be mounted or otherwise disposed between the cornea and the objective lenses. In some embodiments, materials other than glass may be used, including transparent and/or translucent materials; for example plastic lenses may be used in place of any of the glass lenses of the present disclosure; as another example, plastic windows may be used in place of any of the glass windows of the present disclosure.

Figure 5A:
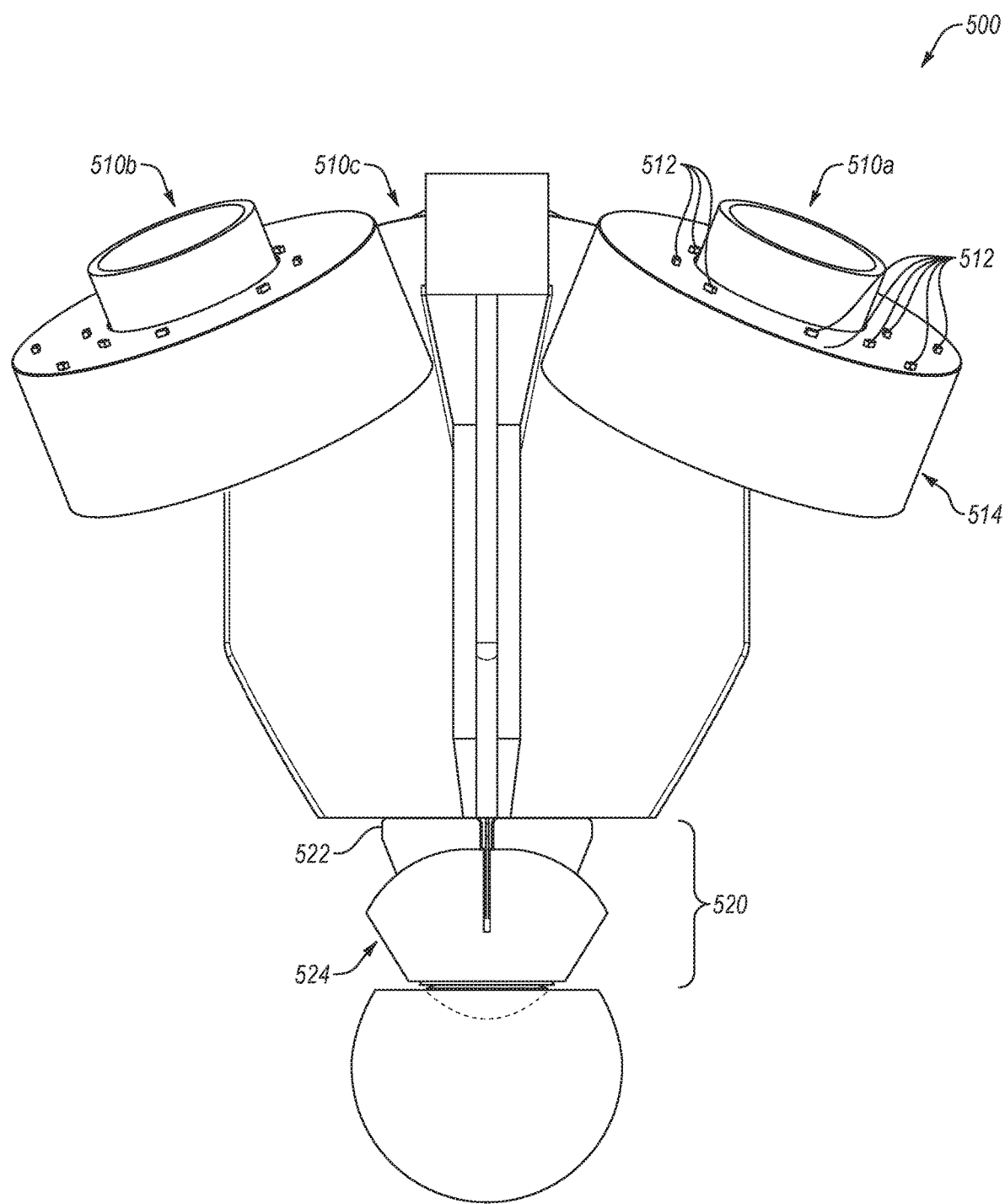
Figure 5B:
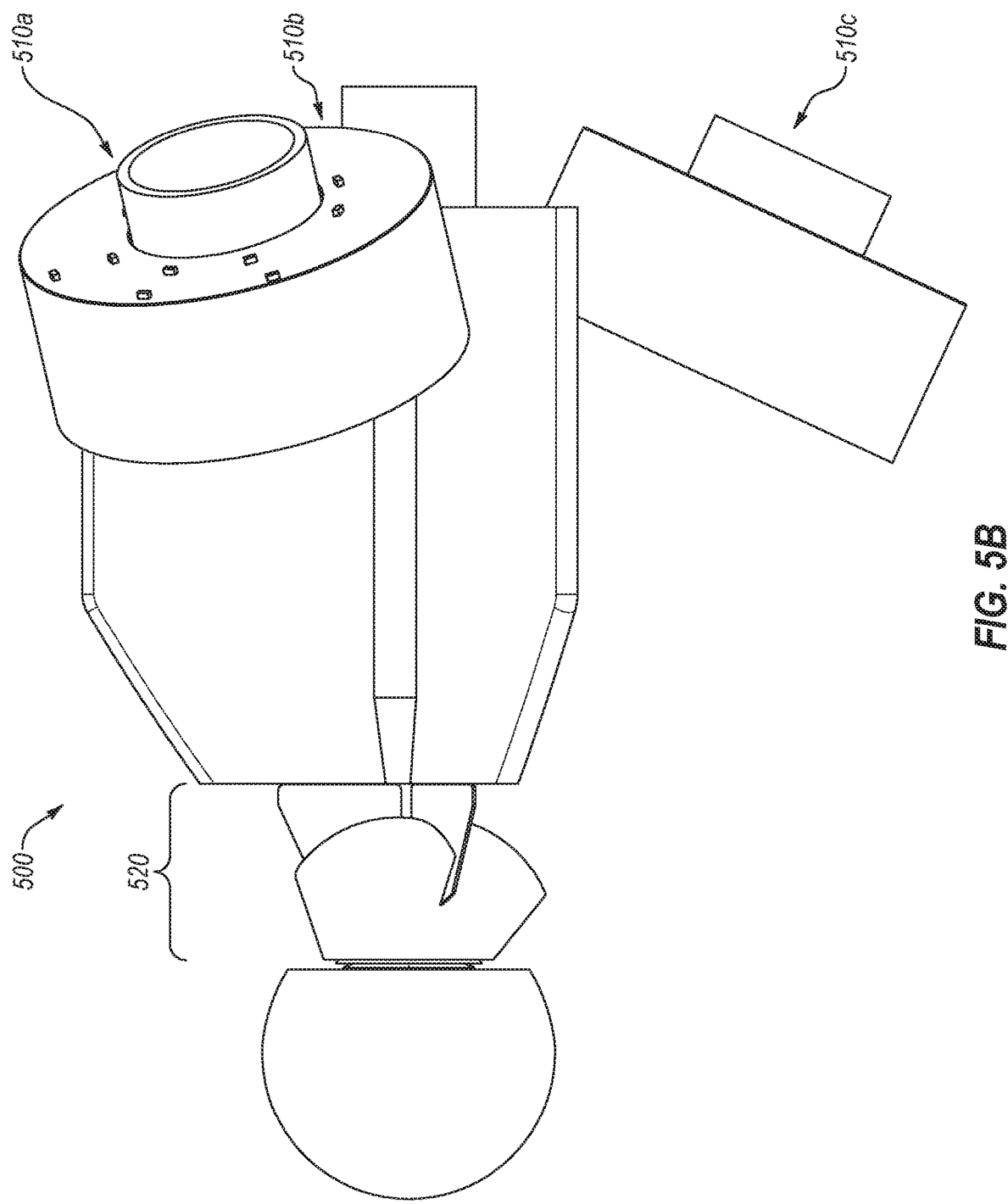

FIGS. 5A-5D illustrate various aspects of an illumination system associated with the multi-channel imaging system 500. Each channel utilizes an illuminating system to facilitate illuminating the posterior segment of the eye for imaging. FIG. 5A illustrates a top down view of the multi-channel imaging system 500, FIG. 5B illustrates a side view of the multi-channel imaging system 500, FIG. 5C illustrates a front view of the multi-channel imaging system 500 (e.g., from the eye looking out towards the multi-channel imaging system 500), and FIG. 5A illustrates a back view of the multi-channel imaging system 500 (e.g., looking towards the eye from the back of the multi-channel imaging system 500). As illustrated in FIGS. 5A-5D, each respective channel includes an illuminating portion 510 (such as the illuminating portions 510a, 510b, and 510c). The illuminating portions 510 include LEDs 512, or any other light emitting element. Additionally, the illuminating portions may include one or more lenses or filters 514 for aligning, shaping, and/or directing the light emitted from the LEDs 512. In some embodiments, the filter 514 may include a polarizing filter such that the illumination light directed towards the eye may be polarized in the same direction to allow filtering of certain undesirable polarizations of light, such as specular reflections from the objective lenses (e.g., the glass lenses 524). Stated another way, by polarizing the illumination light, any reflectance from the lenses or other elements of the imaging device would retain their polarization and thus be filterable by a polarizing filter in the imaging channel (e.g., the cleanup polarizer 356 in FIG. 3), while allowing the scattered illumination on the retina that is travelling back along the imaging channel and thus used in imaging the posterior segment of the eye to pass through the polarizing filter. In some embodiments, polarization may be left out of the design of an imaging device and scattered light may be managed by other means, such as in the optical design of the imaging device or in software post-processing of the images acquired.

In some embodiments, the camera sensor and/or aperture may be oriented directly in line with the center line of the illuminating portion 510. In these and other embodiments, the camera sensor may be located within a cylindrical chamber, and the LEDs 512 may be located outside of the cylindrical chamber. In these and other embodiments, the walls of the cylindrical chamber may act to prevent the illumination from the LEDs 512 from bleeding into the image capturing of the camera device. Stated another way, the LEDs 512 may be located offset from the center line of the illuminating portion 510 while the camera sensor is in line with the center line.

FIGS. 5A-5D illustrates a three-section wall 522 (that may be similar or comparable to the three-section wall 420 of FIG. 4D) and the glass lenses 524 (that may be similar or comparable to the lenses and/or windows 352 and/or 354 of FIG. 3) within a nose cone portion 520 of the imaging device.

Using the imaging devices 510, various portions of the posterior segment of the eye may be illuminated at different times and along different paths to avoid illumination light interfering with the imaging path. For example, overlap between the illumination path to the posterior segment and an imaging path back from the posterior segment may cause diffuse scatter from ocular surfaces which may present as haze in a captured image.

Figure 6C:
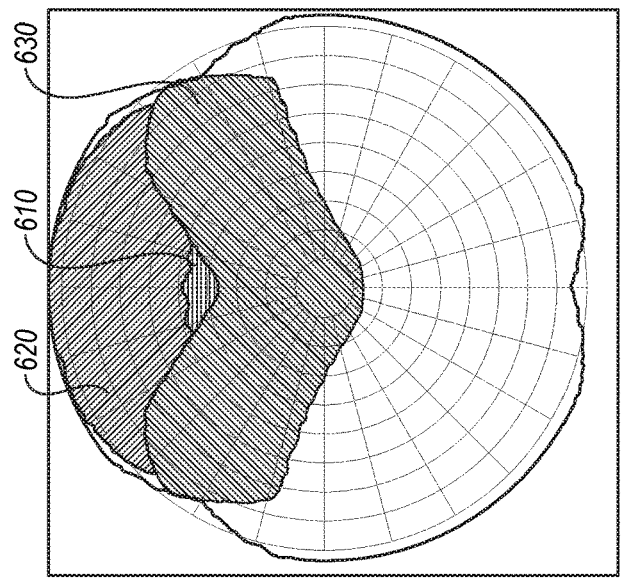
FIGS. 6A-6C illustrate example illumination patterns of a given region of the posterior segment of the eye for imaging.
Figure 6B:
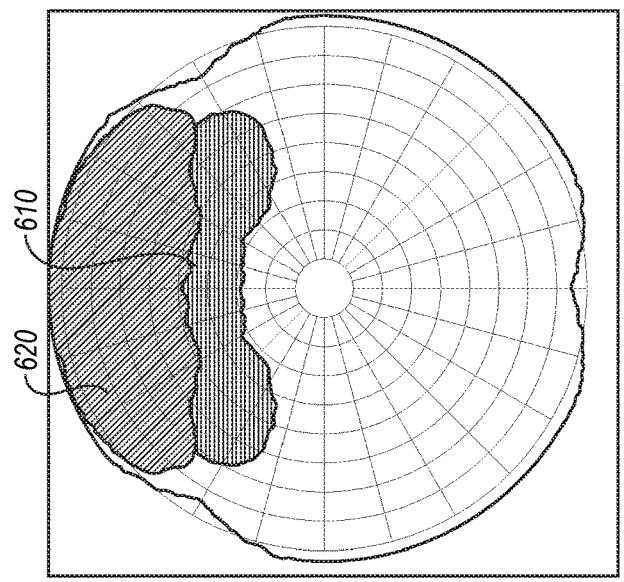
Figure 6A:
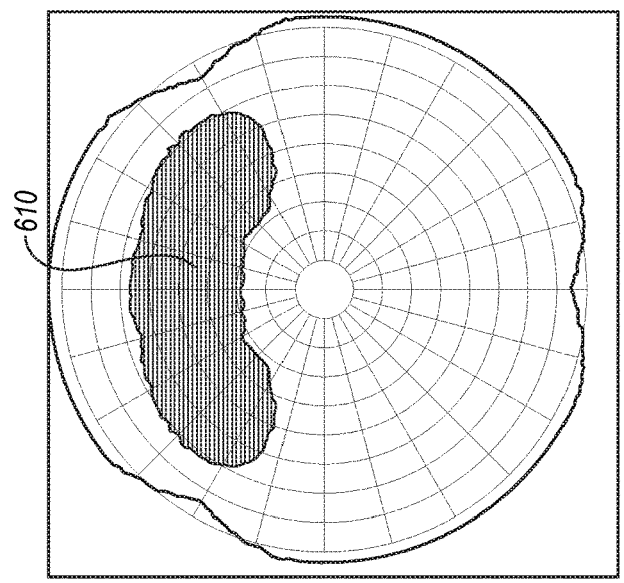

FIGS. 6A-6C illustrate illumination patterns of a given region of the posterior segment of the eye for imaging. The gridlines represent the same gridlines as used in FIGS. 1A-1B. The dark blue region represents the various regions covered by the field-of-view illustrated in FIGS. 1A-1B. FIGS. 6A-6C illustrate how various portions of a given region may be illuminated by different illuminating elements to avoid contamination of the imaging path by the illumination path. By illuminating different regions at different times, each portion may be illuminated separately and the images may be combined to cover the entire region, and thus the entire wide field-of-view. The grid lines in FIGS. 6A-6C illustrate the posterior segment projected outward from the fovea. An inner radial portion 610 may illuminate from approximately 30-60 degrees from the fovea, an outer radial portion 620 may illuminate from approximately 50-90 degrees from the fovea, and a medial portion 630 may illuminate from approximately minus 15-positive 40 degrees from the fovea, as well as the overlapping regions between the channels (e.g., regions 140, 142, 144, and 150 of FIG. 1).

The various portions 610, 620, and 630 may be illuminated and oriented in a different manner than illustrated in FIGS. 6A-6C that avoids interference on both the posterior and anterior surfaces of the crystalline lens and cornea of the eye that would interfere with the imaging channel of the portion being illuminated and imaged. In some embodiments, the various portions 610, 620, and 630 may be illuminated one at a time for all three channels at the same time (e.g., the inner radial portion 610 for all three channels while an image is captured, the outer radial portion 620 for all three channels while an image is captured, and the medial portion 630 for all three channels while an image is captured), separately (e.g., the inner radial portion 610 for one channel may be illuminated while an image is captured for the illuminated portion of the posterior segment by one of the channels, etc.), or any combination or variation thereof.

Figure 7:
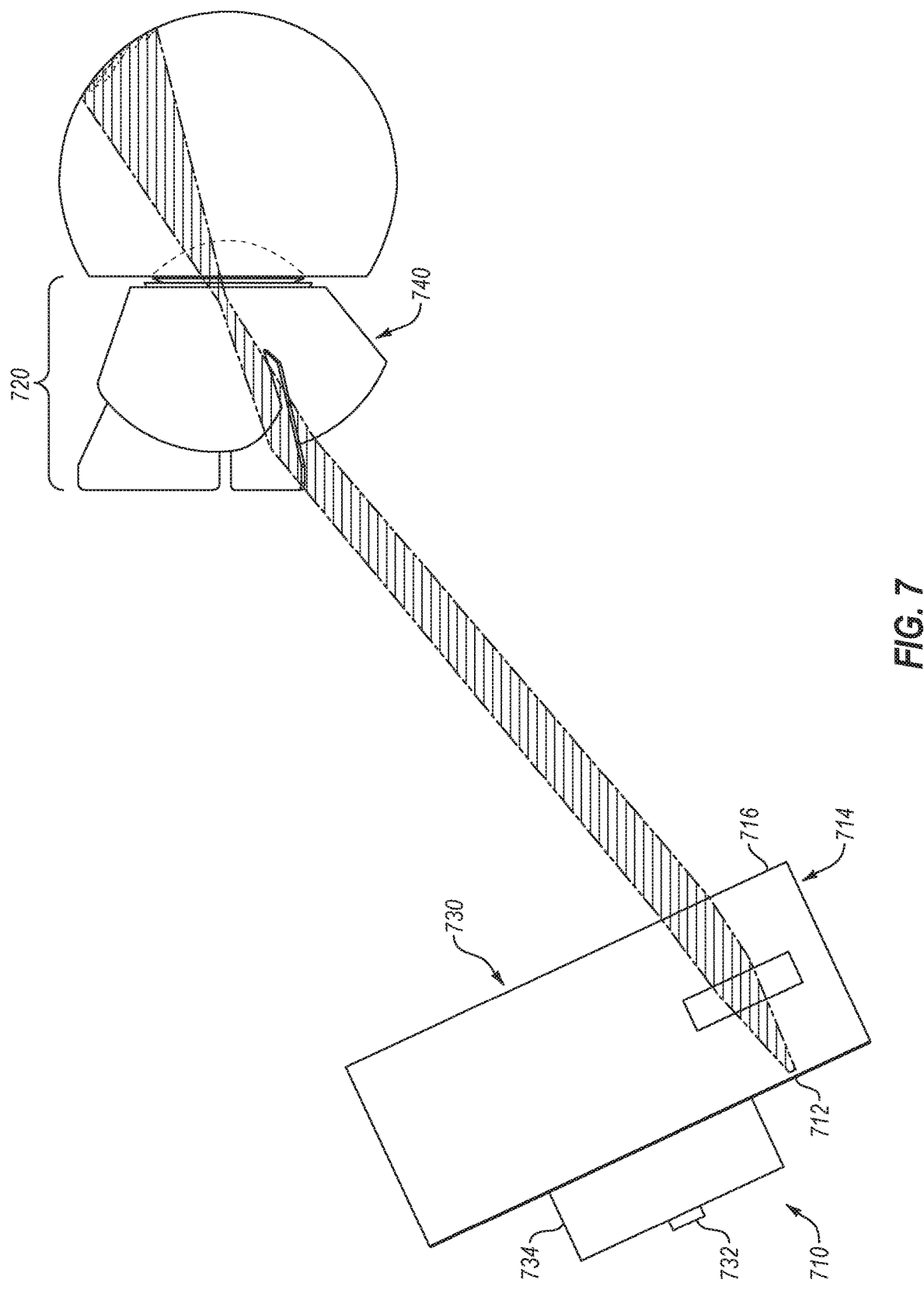
FIG. 7 illustrates an example of an illumination system for illuminating an inner radial portion of the posterior segment of the eye.

FIG. 7 illustrates an example of illumination system 700 for illuminating an inner radial portion of the posterior segment of the eye. The illumination system 700 may include a base component 710 and a nose cone component 720.

As illustrated in FIG. 7, the base component 710 may include an LED 712 (or other light emitting device) and an associated aperture. The base component 710 may also include an illumination condenser system 714, and a baffle and prepolarizer 716. The base component 710 may additionally include a camera component 730 with a camera sensor 732 and a casing 734. The camera sensor 732 may be disposed within the casing 734, which may function to prevent light from the LED 712 from impacting the image capturing by the camera sensor 732.

In some embodiments, the illumination condenser system 714 may include two elements (e.g., four surfaces) patterned symmetrically about the plane bisecting the imaging channel and retina. In these and other embodiments, the illumination condenser system 714 may include one or more passive refractive or reflective optical elements, or active elements, such as a reflective MEMS micromirror array, or transmissive spatial light modulator, to enable beam control and steering.

As illustrated in FIG. 7, the plane in which the LED 712 is positioned and the illumination condenser system 714 may be positioned orthogonal to the channel axis (e.g., the axis along which the optical traces of the imaging channel are directed to the camera sensor 732), such that the plane in which the LED 712 is positioned and the illumination condenser system 714 may be mounted around the casing 734. It will be appreciated that the LED 712 and the illumination condenser system 714 may be placed anywhere in space such that the illumination path for the inner radial segment does not interfere with the imaging path for that segment on any ocular surfaces.

In some embodiments, the illumination condenser system 714 may be aligned and configured to image the cornea to the aperture plane. In these and other embodiments, such an imaging location may further be based on the properties of an objective lens system 740 (which may be similar or comparable to the glass lenses 524 of FIG. 5). For example, as illustrated in FIG. 7, the illumination rays may travel through the illumination condenser system to be directed by the objective lens system 740 such that the illumination is approximately at its narrowest point in the cornea, thus reducing and/or minimizing interference with the rays of the imaging channel passing back through the cornea. While articulated in terms of the illumination rays imaging at the cornea, the LED 712 and associated aperture, the illumination condenser system 714, and/or the objective lens system 740 may be configured such that the illumination rays may be configured to image at any location between the cornea and the posterior crystalline lens of the eye along an axis that is non-overlapping with the imaging path for the radial segment being illuminated. In these and other embodiments, the aperture size and/or position of the aperture associated with the LED 712 may be selected to confine the path of the illumination rays through an exit pupil such that the illumination rays do not interfere with the path of the imaging rays when imaging the portion and/or region of the posterior segment that is being imaged.

In some embodiments, the baffles associated with the illumination channel may be placed and/or configured to trap stray light on the posterior (e.g., on the other side of the illumination condenser system 714 from the LED 712) and anterior (e.g., on the same side as the LED 712) sides of the illumination condenser system 714. Additionally or alternatively, the baffles may be placed and/or configured to trap stray light between elements in the illumination condenser system 714. In some embodiments, the baffles may be moveable within the device 700. For example, the baffles may be mechanized and/or motorized such that their position may be adjusted to alter the illumination optics for different eyes and/or different applications. In some embodiments, the casing 734 may function as a baffle to trap such stray light. Additionally or alternatively, the three-section wall of the imaging device may operate as a baffle to block certain stray light (e.g., the three-section wall 420 of FIGS. 4A-4D).

In some embodiments, the pre-polarizer 716 may be configured to polarize the incident illumination light to facilitate filtering. For example, by polarizing the illumination light, any specular reflections (e.g., from the objective lens system 740) maintain their state of polarization. Such an arrangement allows a cleanup polarizer in the imaging path to reject specularly reflected light as such light maintains polarization on reflection (e.g., may be filtered by the cleanup polarizer 356). Additionally, such an arrangement may permit non-polarized light, such as the illumination light scattered by the retina tissue and travelling along the imaging channel, to pass through the cleanup polarizer for imaging.

Figure 8B:
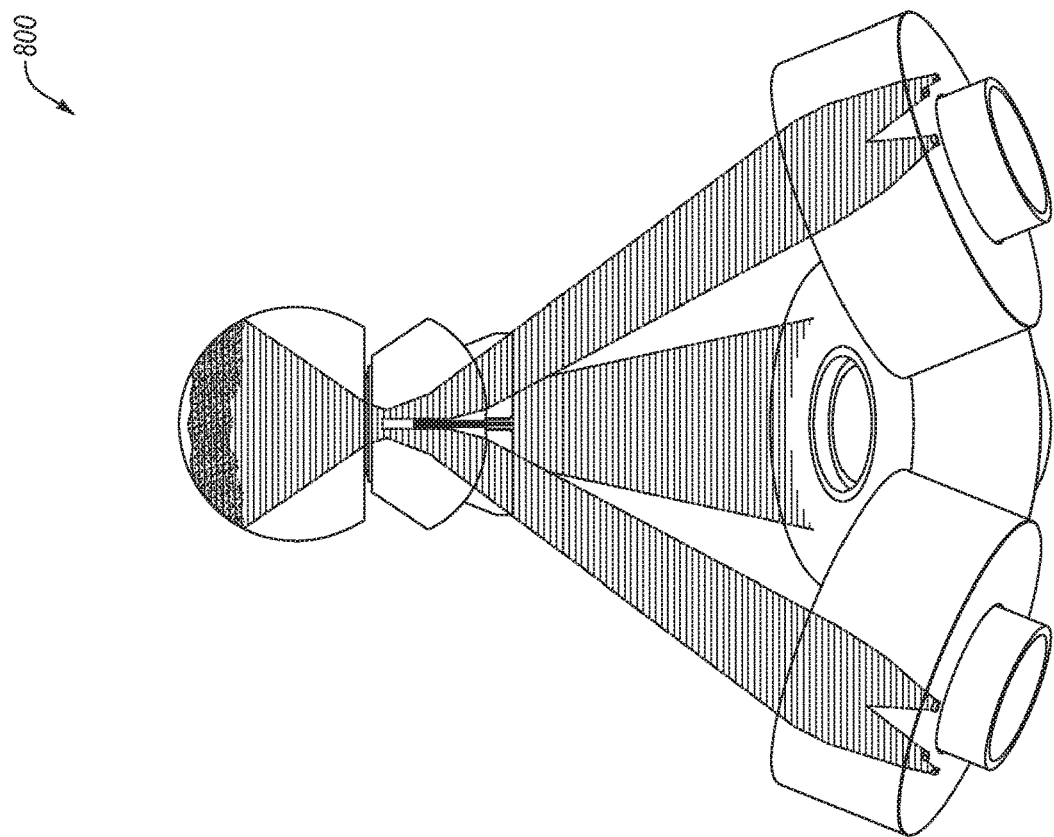
FIGS. 8A-8D illustrate a device generating imaging rays for illuminating the inner radial portion of the posterior segment of the eye.
Figure 8A:
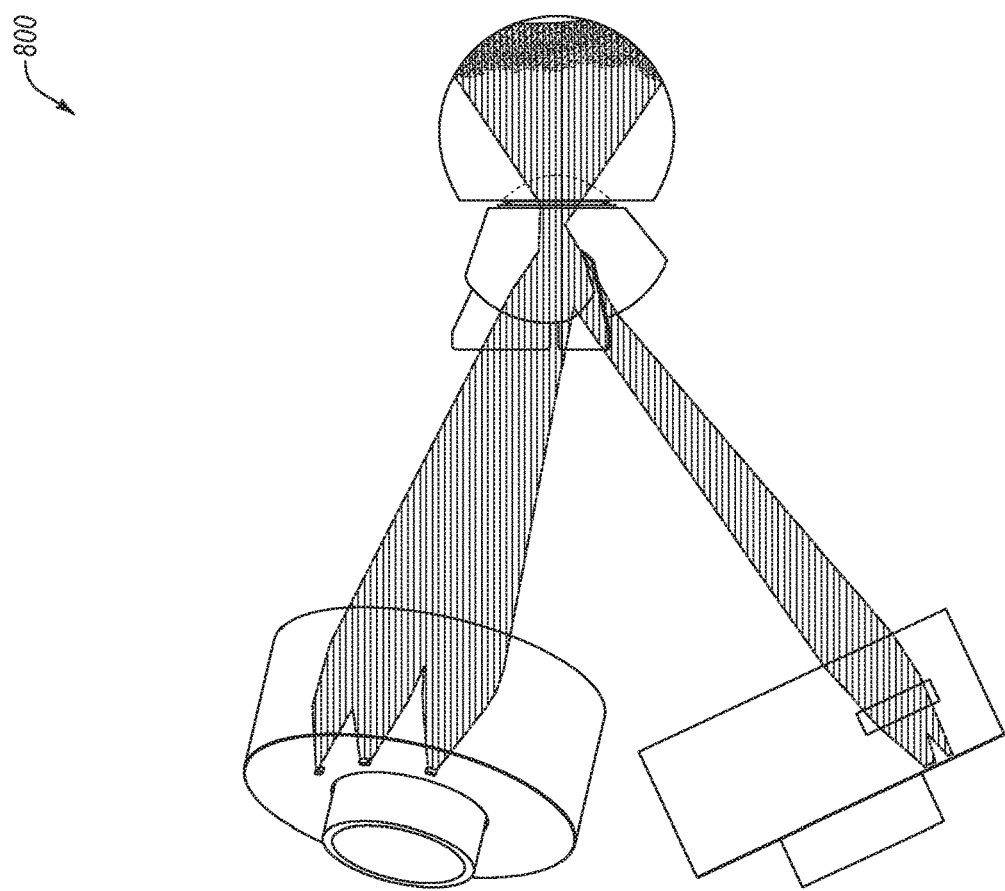
Figure 8D:
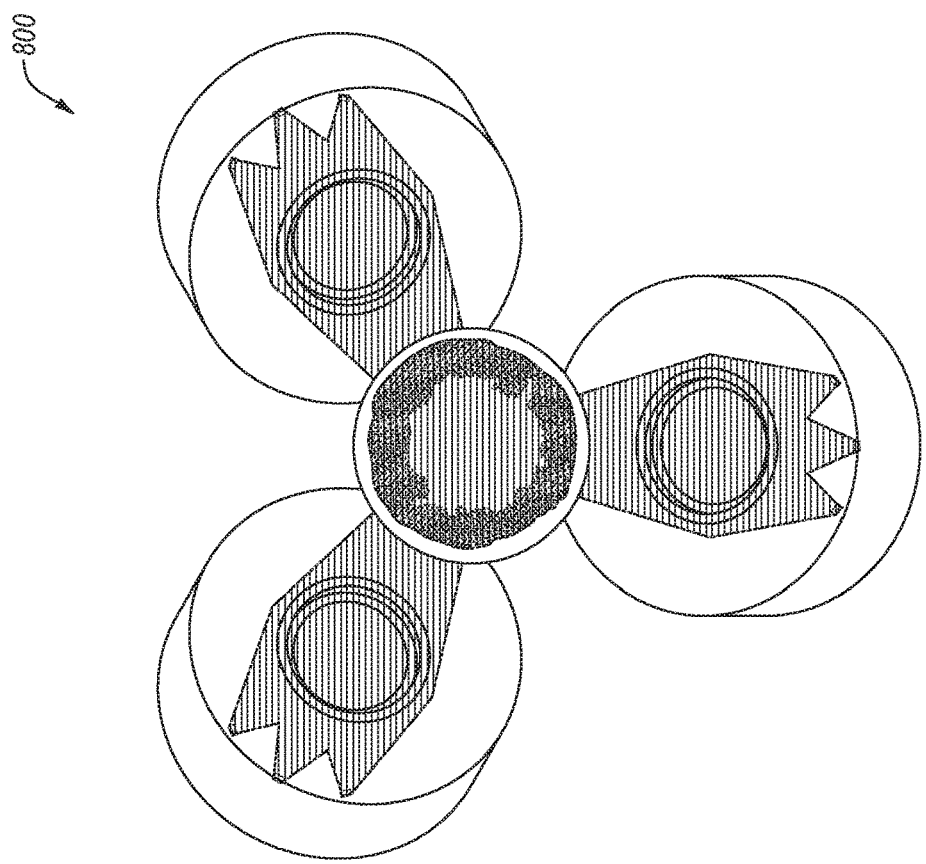
Figure 8C:
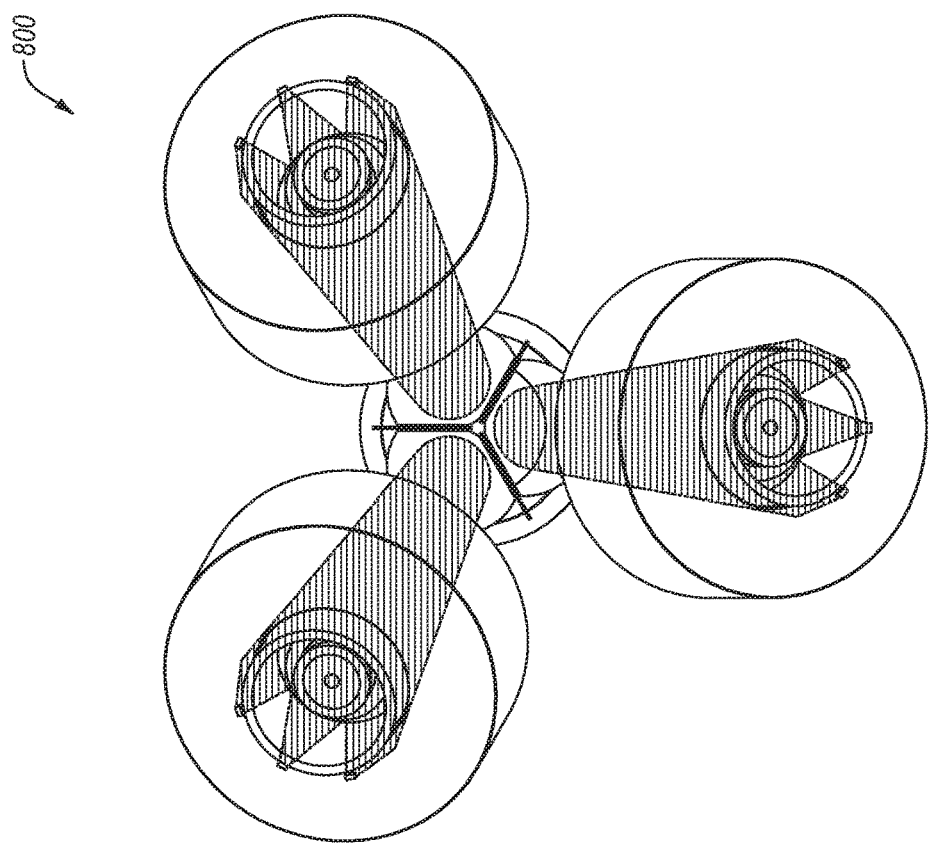

FIGS. 8A-8D illustrate the imaging system 800 generating the imaging rays for illuminating the inner radial portion of the posterior segment. FIG. 8A illustrates a side view of the imaging system 800, FIG. 8B illustrates a top-down view of the imaging system 800, FIG. 8C illustrates a front view of the imaging system 800 (e.g., from the eye looking out towards the multi-channel imaging system), and FIG. 8D illustrates a back view of the multi-channel imaging system 800.

As illustrated in FIGS. 8A-8D, in some embodiments, all three channels may illuminate simultaneously such that the inner radial portions for all three imaging channels may be illuminated at the same time. For example, all three imaging channels may illuminate and image all three imaging channels at the inner radial portion of the posterior segment at the same time. Additionally or alternatively, the inner radial portion for each imaging channel may be independently or sequentially illuminated and imaged, for example, three distinct images for each of the inner radial portions for each of the imaging channels may be taken at different times.

Figure 9:
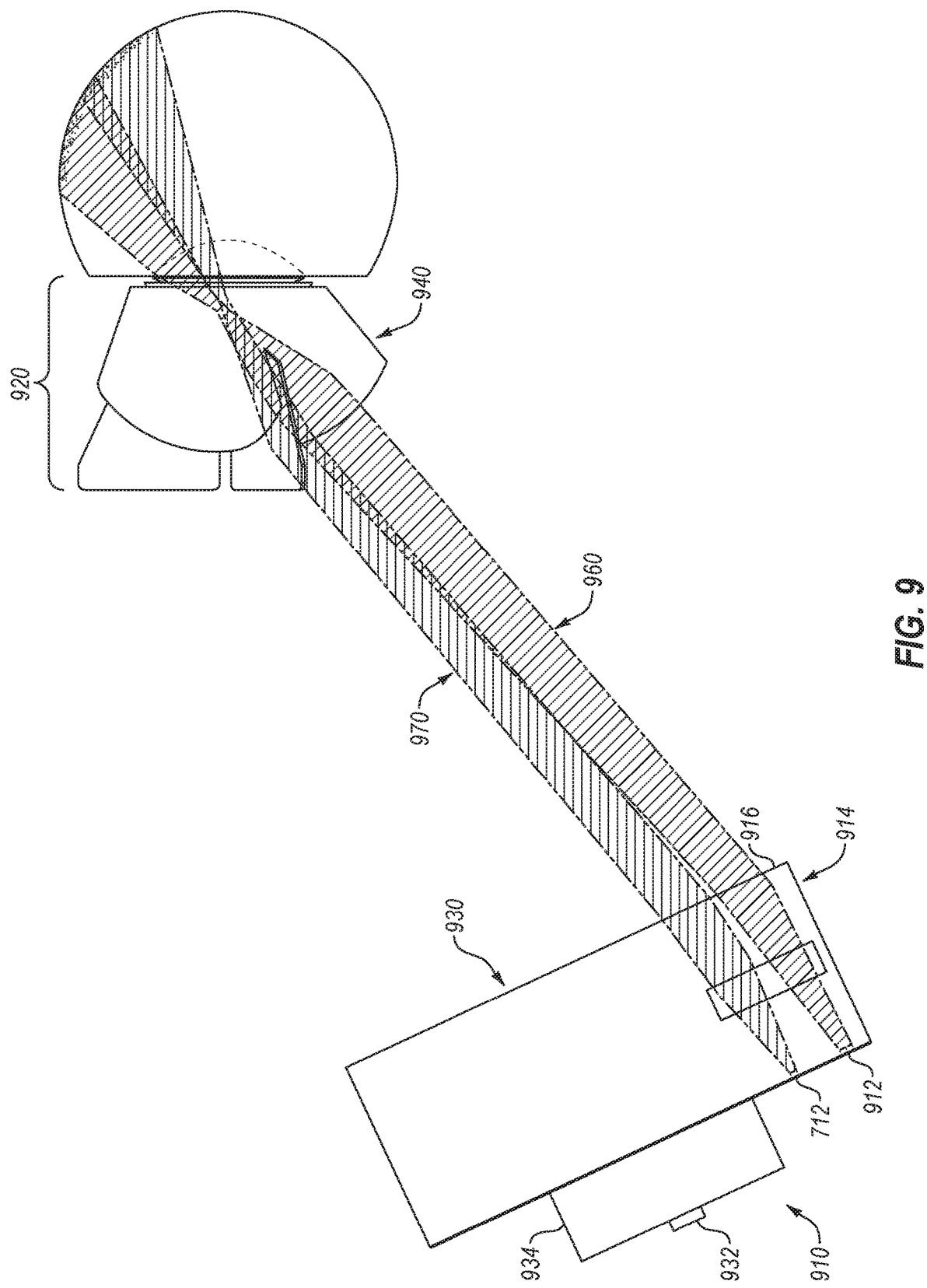
FIG. 9 illustrates an example of a device for illuminating an inner radial portion and an outer radial portion of the posterior segment of the eye.

FIG. 9 illustrates an example of illumination system 900 for illuminating an inner radial portion and an outer radial portion of the posterior segment of the eye. The illumination system 900 may include a base component 910 and a nose cone component 920. The illumination system 900 may be similar or comparable to the illumination system 700 illustrated in FIG. 7. The illumination system 900 may include a distinct LED 912 and associated aperture that may be different or distinct from the LED 712 of FIG. 7, where the LED 912 may be configured to illuminate the outer radial portion and the LED 712 may be configured to illuminate the inner radial portion of the posterior segment. In these and other embodiments, the illumination system 900 may include all of the components illustrated in FIG. 7 as well as those illustrated in FIG. 9, such that the illumination system 900 may illuminate the inner radial segment and the outer radial segment. The components that are similarly numbered may operate or function in the same or similar manner as the components as described above with respect to FIG. 7.

The elements of FIG. 9 may be similar or comparable to those of FIG. 7, serving similar functions although illuminating a different portion of the posterior segment of the eye. For example, the base component 910 may be similar or comparable to the base component 710 of FIG. 7 (e.g., may include an LED 912 similar or comparable to the LED 712 (or other light emitting device) and an associated aperture). The base component 910 may also include an illumination condenser system 914 that may be similar or comparable to the illumination condenser system 714. The base component 910 may also include a baffle and/or prepolarizer 916 that may be similar or comparable to the baffle and/or prepolarizer 716. The base component 910 may additionally include a camera component 930 that may be similar or comparable to the camera component 730, including a camera sensor 932 comparable or similar to the camera sensor 732 and casing 934 similar or comparable to the casing 734.

As illustrated in FIG. 9, the illumination beams 960 illuminating the outer radial segment and the illumination beams 970 illuminating the inner radial segment are illustrated as being active simultaneously. As seen in FIG. 9, the combination of the illumination beams 960 and 970 consume more space within the anterior segment of the eye, increasing the likelihood of illumination interfering with imaging of the posterior segment of the eye. In these and other embodiments, if the orientation and/or alignment of the illumination beams 960 and 970 (e.g., via the apertures, illumination condenser system 914, and/or objective lens system 940) is such that both segments may be imaged without interference in the imaging channel, both may be simultaneously illuminated and imaged. Additionally or alternatively, the inner radial segment and the outer radial segment may be sequentially illuminated such that the two segments may be independently imaged where a smaller portion of the space within the anterior segment of the eye is consumed by the illumination beams.

Figure 10B:
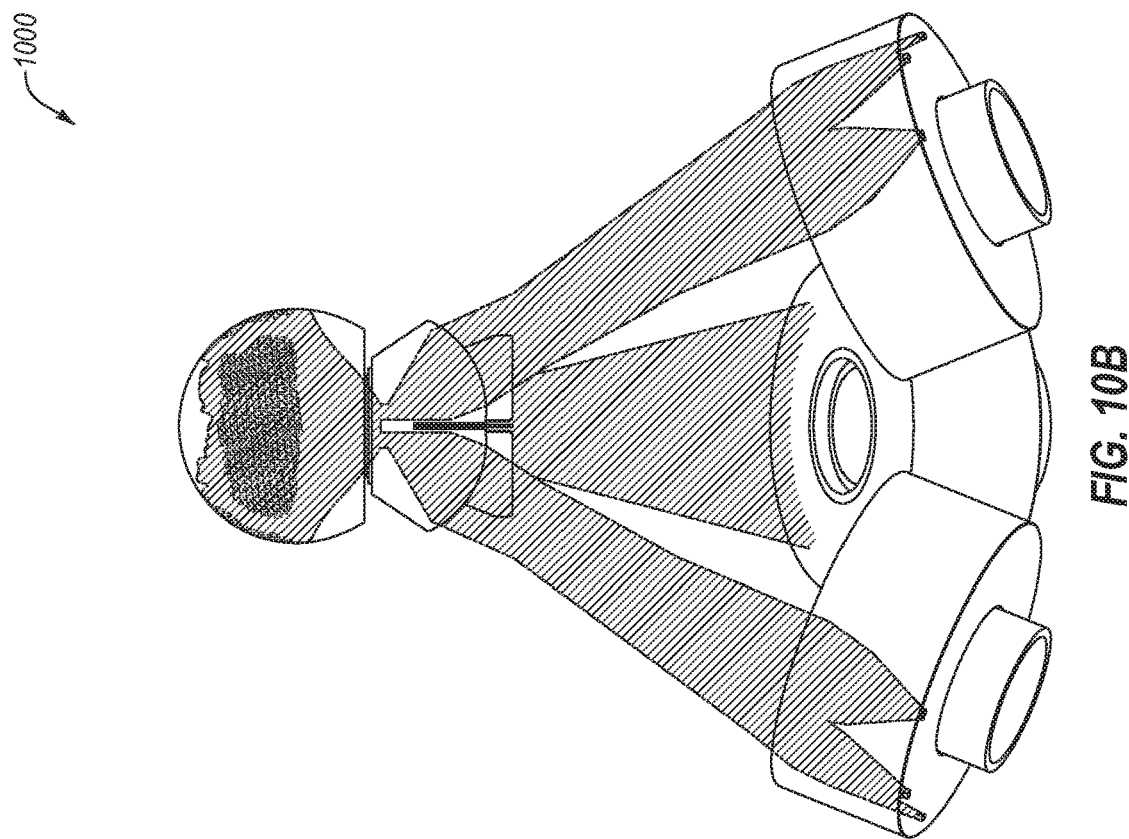
FIGS. 10A-10D illustrate an example a device generating imaging rays for illuminating the outer radial portion of the posterior segment of the eye.
Figure 10A:
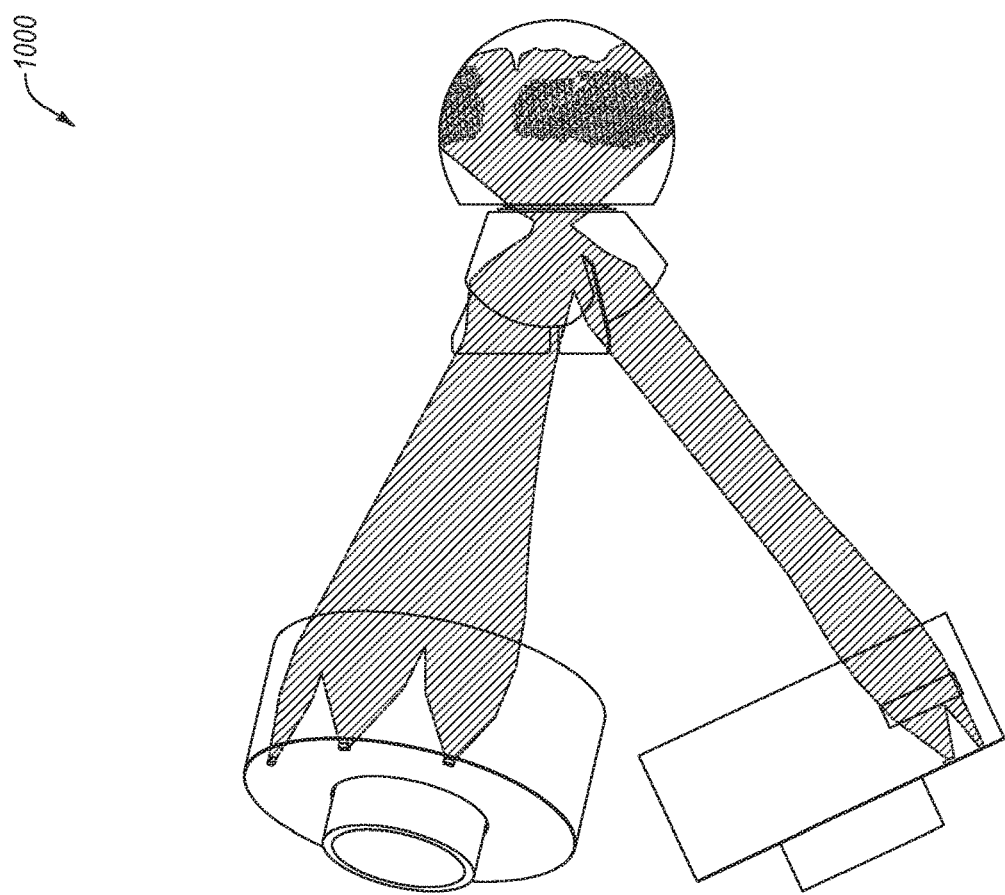
Figure 10D:
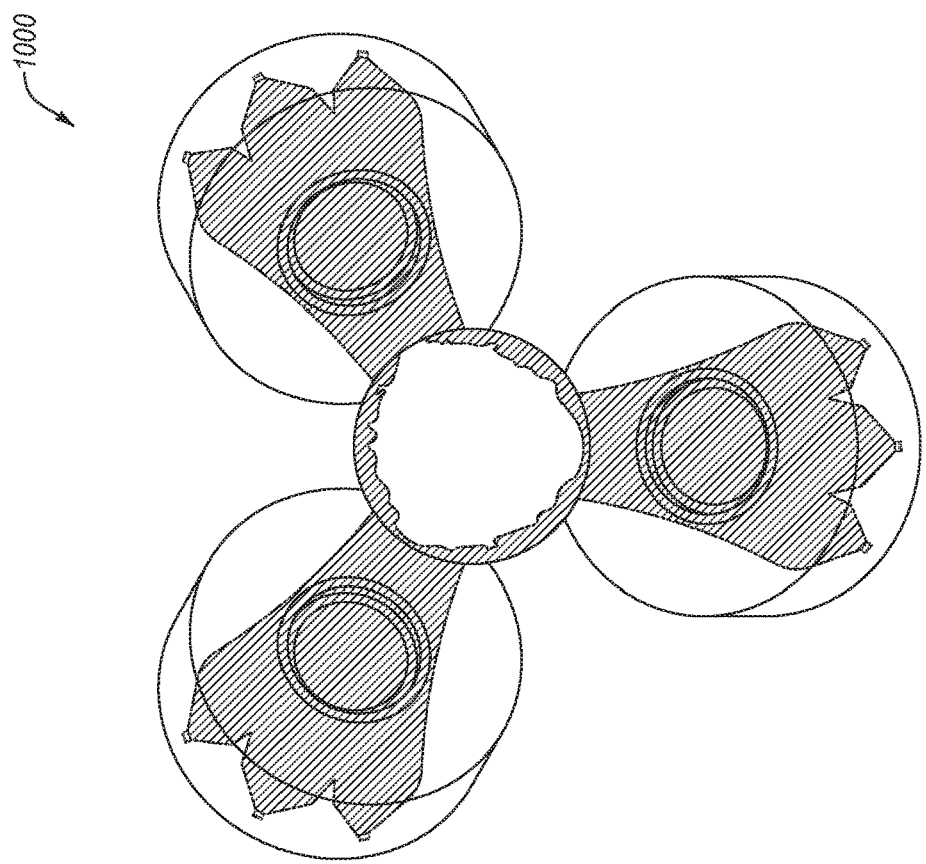
Figure 10C:
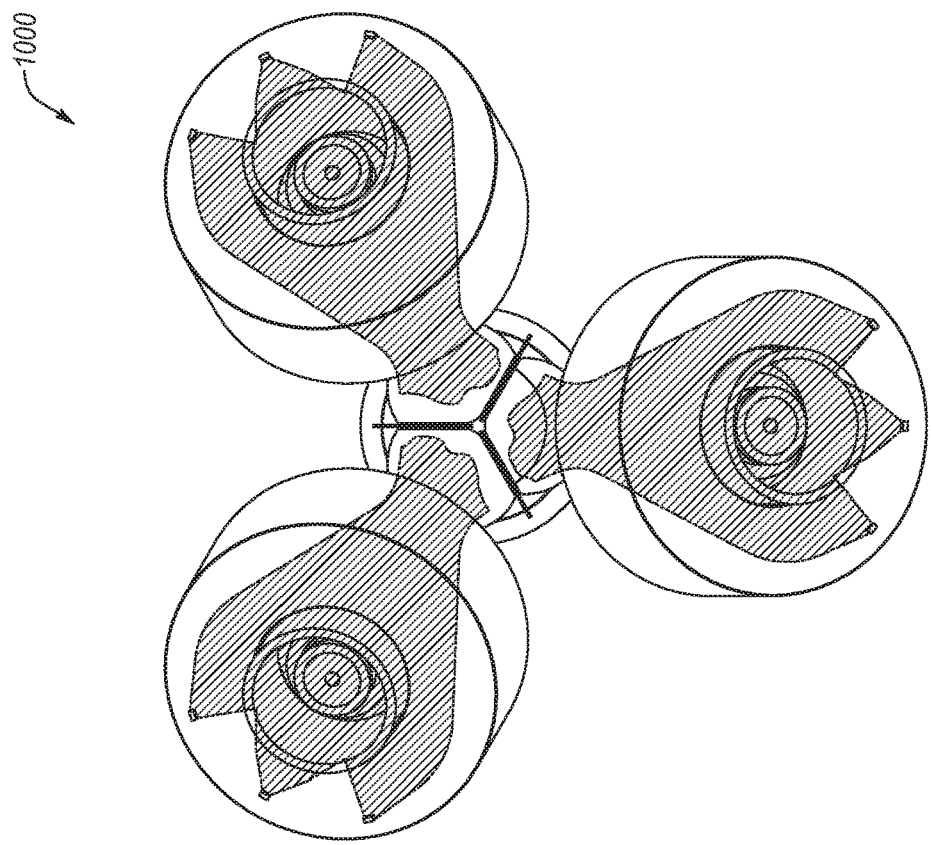

FIGS. 10A-10D illustrate the imaging system 1000 generating the imaging rays for illuminating the outer radial portion of the posterior segment. FIG. 10A illustrates a side view of the imaging system 1000, FIG. 10B illustrates a top-down view of the imaging system 1000, FIG. 10C illustrates a front view of the imaging system 1000 (e.g., from the eye looking out towards the multi-channel imaging system), and FIG. 10D illustrates a back view of the multi-channel imaging system 1000.

As illustrated in FIGS. 10A-10D, in some embodiments, all three channels may illuminate simultaneously such that the outer radial portions for all three imaging channels may be illuminated at the same time. For example, all three imaging channels may illuminate and image all three imaging channels at the outer radial portion of the posterior segment at the same time. Additionally or alternatively, the outer radial portion for each imaging channel may be independently or sequentially illuminated and imaged, for example, three distinct images for each of the outer radial portions for each of the imaging channels may be taken at different times.

Figure 11B:
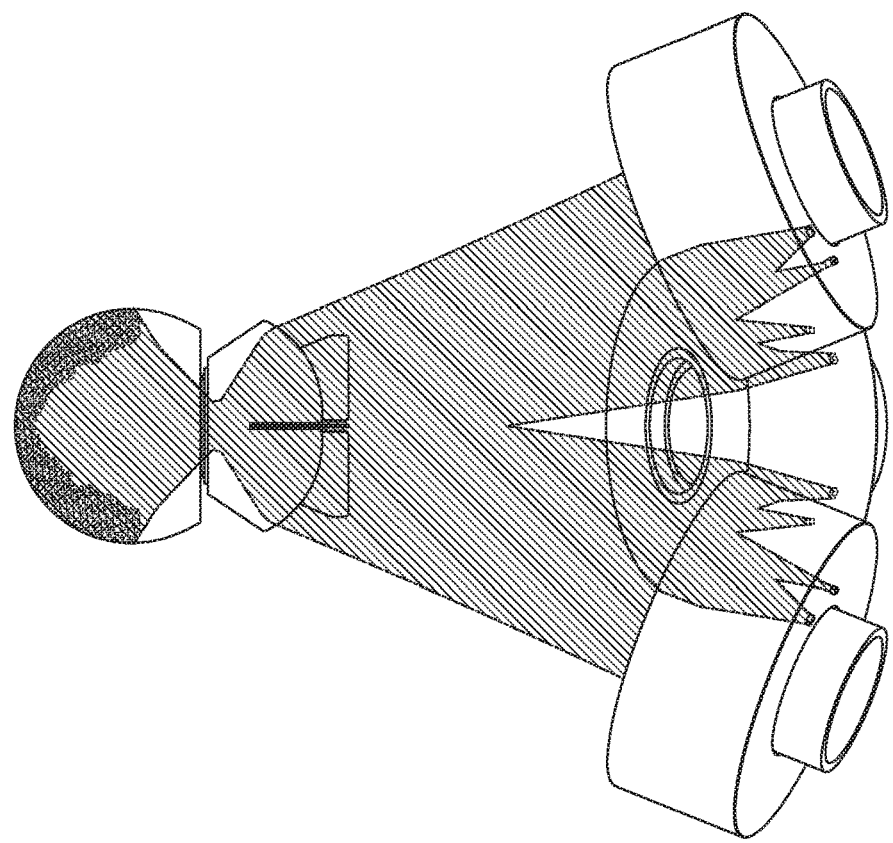
FIGS. 11A-11D illustrate an example device generating imaging rays for illuminating the medial portion of the posterior segment of the eye.
Figure 11A:
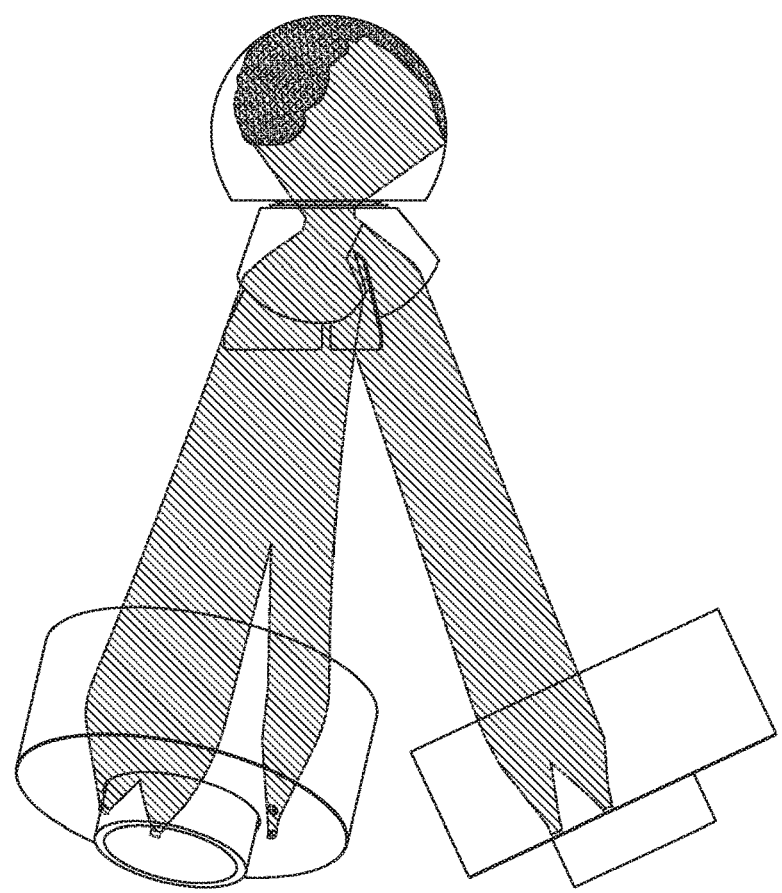
Figure 11D:
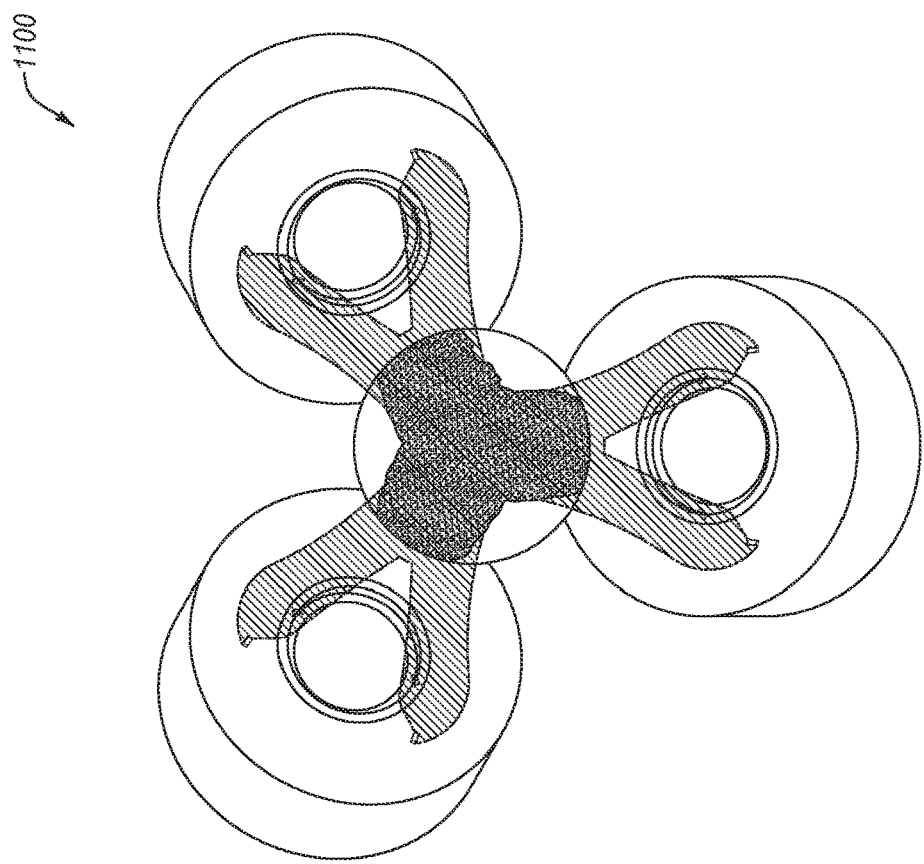
Figure 11C:
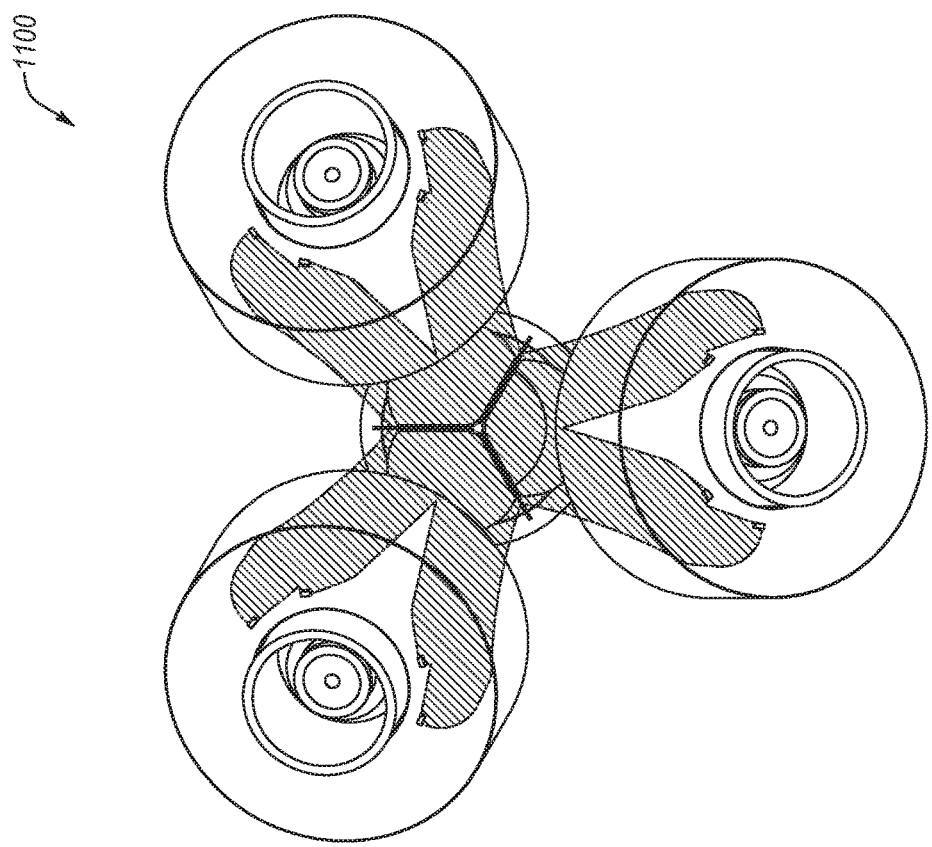

FIGS. 11A-11D illustrate the imaging system 1100 generating the imaging rays for illuminating the medial portion of the posterior segment. FIG. 11A illustrates a side view of the imaging system 1100, FIG. 11B illustrates a top-down view of the imaging system 1100, FIG. 11C illustrates a front view of the imaging system 1100 (e.g., from the eye looking out towards the multi-channel imaging system), and FIG. 11D illustrates a back view of the multi-channel imaging system 1100.

As illustrated in FIGS. 11A-11D, in some embodiments, all three channels may illuminate simultaneously such that the medial portions for all three imaging channels may be illuminated at the same time. For example, all three imaging channels may illuminate and image all three imaging channels at the medial portion of the posterior segment at the same time. Additionally or alternatively, the medial portion for each imaging channel may be independently or sequentially illuminated and imaged, for example, three distinct images for each of the medial portions for each of the imaging channels may be taken at different times.

In these and other embodiments, the imaging system 1100 for the medial segment may include and/or utilize a similar or comparable illumination condenser system such as those illustrated in FIGS. 7 and 9. Additionally or alternatively, the imaging system 1100 for the medial segment may include and/or utilize a baffle and/or prepolarizer of FIGS. 7 and 9.

In some embodiments, a given medial portion may be illuminated by two neighboring channels, rather than the actual imaging channel. For example, with a three channel imaging system, as an initial channel images, the other two channels may illuminate the medial portion as it is imaged by the initial channel. In these and other embodiments, a series of images may be captured as one channel images and the other two channels illuminate in a rotating or sequential manner. For example, with a first, second, and third channel, the first channel may image while the second and third channels illuminate, followed by the second channel imaging while the first and third channels illuminate, followed by the third channel imaging while the first and second channels illuminate.

Figure 12B:
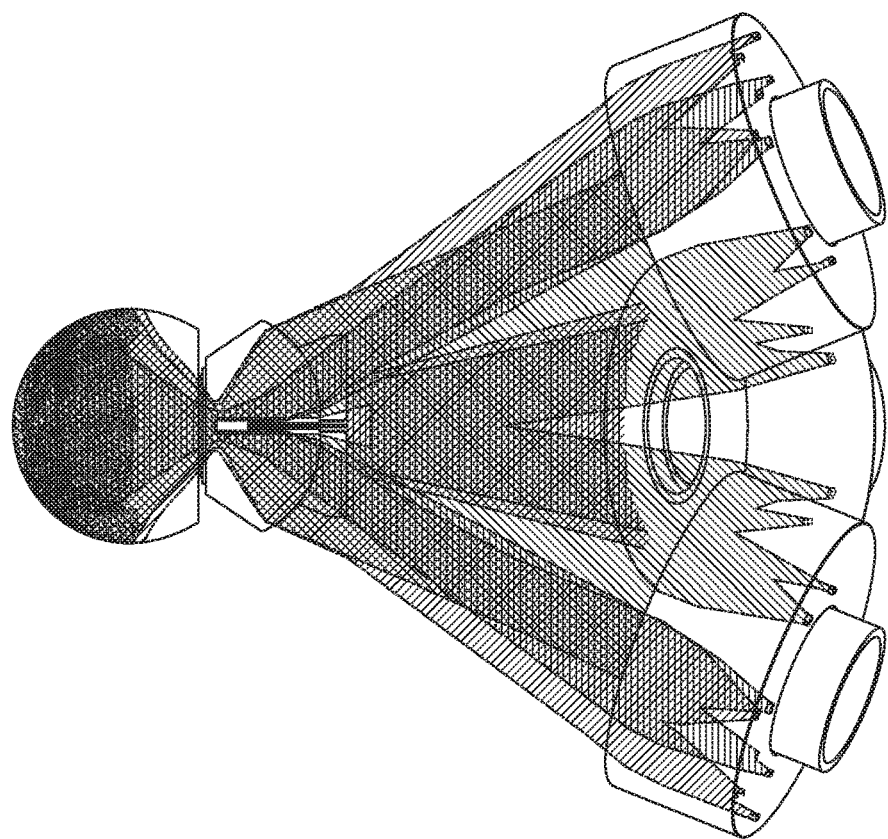
FIGS. 12A-12D illustrate an example device generating imaging rays for illuminating the outer radial portion, the inner radial portion, and the medial portion of the posterior segment of the eye.
Figure 12A:
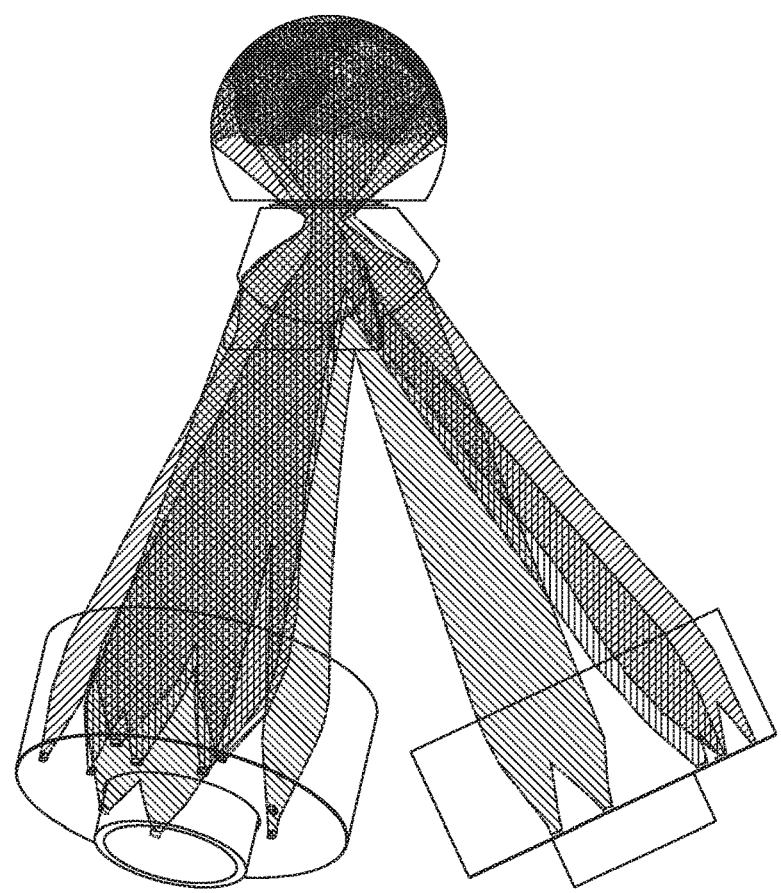
Figure 12D:
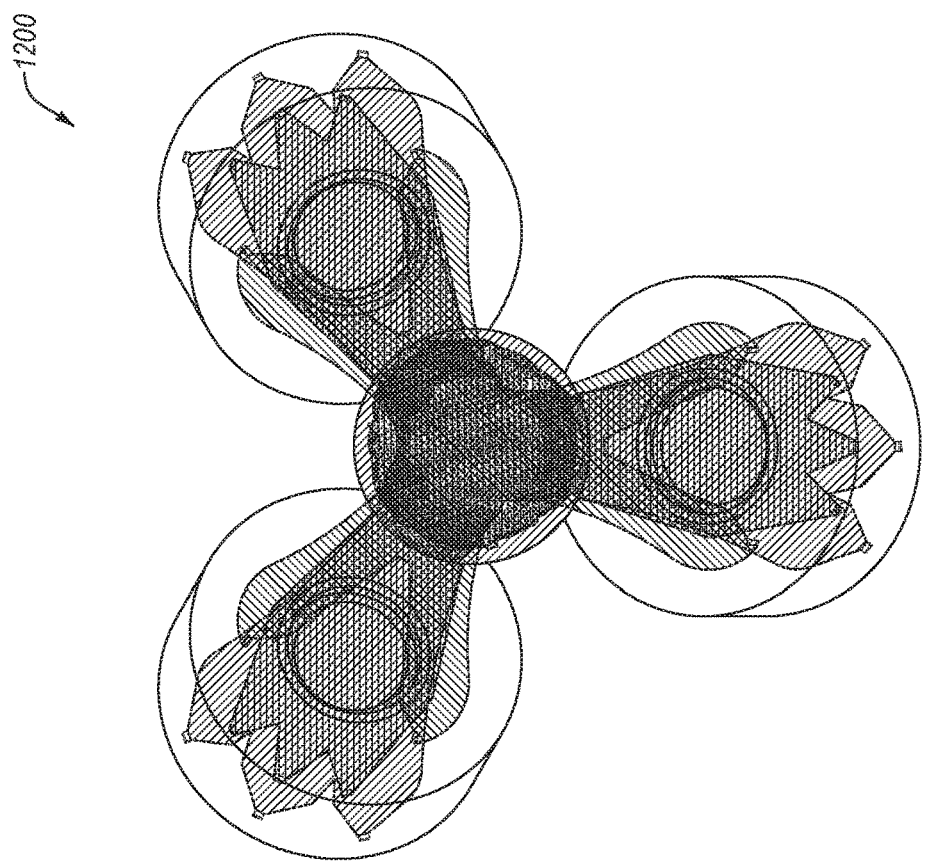
Figure 12C:
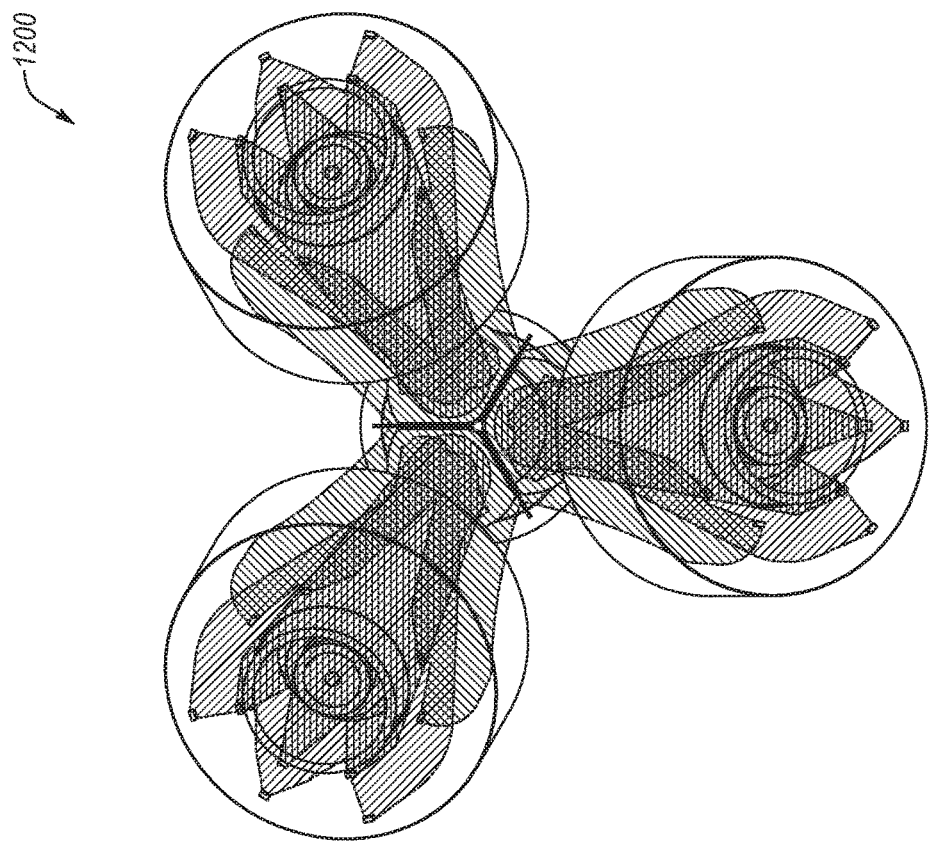

FIGS. 12A-12D illustrate the imaging system 1200 generating the imaging rays for illuminating the outer radial portion, the inner radial portion, and the medial portion of the posterior segment. FIG. 12A illustrates a side view of the imaging system 1200, FIG. 12B illustrates a top-down view of the imaging system 1200, FIG. 12C illustrates a front view of the imaging system 1200 (e.g., from the eye looking out towards the multi-channel imaging system), and FIG. 12D illustrates a back view of the multi-channel imaging system 1200.

As illustrated in FIGS. 12A-12D, rays for illuminating all three portions are illustrated, as well as the rays for imaging the posterior segment. For example, the rays for illuminating the outer radial portion (red), the inner radial portion (green), and the medial portion (magenta) are illustrated in conjunction with the rays for imaging (blue) the posterior segment.

FIGS. 13A-13D illustrates an imaging system 1300 for guiding placement of an associated imaging device relative to the eye. For example, imaging system 1300 may include one or more LEDs 1312 that may be configured to provide reflection and/or scattering from surfaces of the eye, such as the cornea, crystalline lens, and/or retina, such that an operator of an imaging device may orient the imaging device correctly upon the eye. As another example, the imaging system 1300 may include an illumination condenser system 1314 that may direct or shape the guidance illumination. In these and other embodiments, the illumination condenser system 1314 may be bisected by the plane that bisects the imaging channel and the retina. Additionally, the imaging system 1300 may utilize a nose cone section 1320, including an objective lens system 1340, for directing guidance rays 1350 to the center of the eye beginning at equidistant positions about the center of the eye. For example, as illustrated in FIGS. 13A-13D, each of the guidance rays 1350 from each of the three channels may combine near the center of the eye such that the reflectance of each of the multiple guidance rays 1350 may be oriented around the center of the eye by an operator of the imaging system 1300.

In these and other embodiments, the guidance rays 1350 may consume a substantial portion of the space through which the imaging rays may pass in the anterior segment of the eye in order to allow the imaging device to be guided in position with respect to the eye to facilitate imaging. In these and other embodiments, imaging and/or illumination of the retina may occur after the guidance has been completed such that the consumption of the substantial portion of the space does not impact the imaging that occurs after the guidance of the imaging device.

Figure 13A:
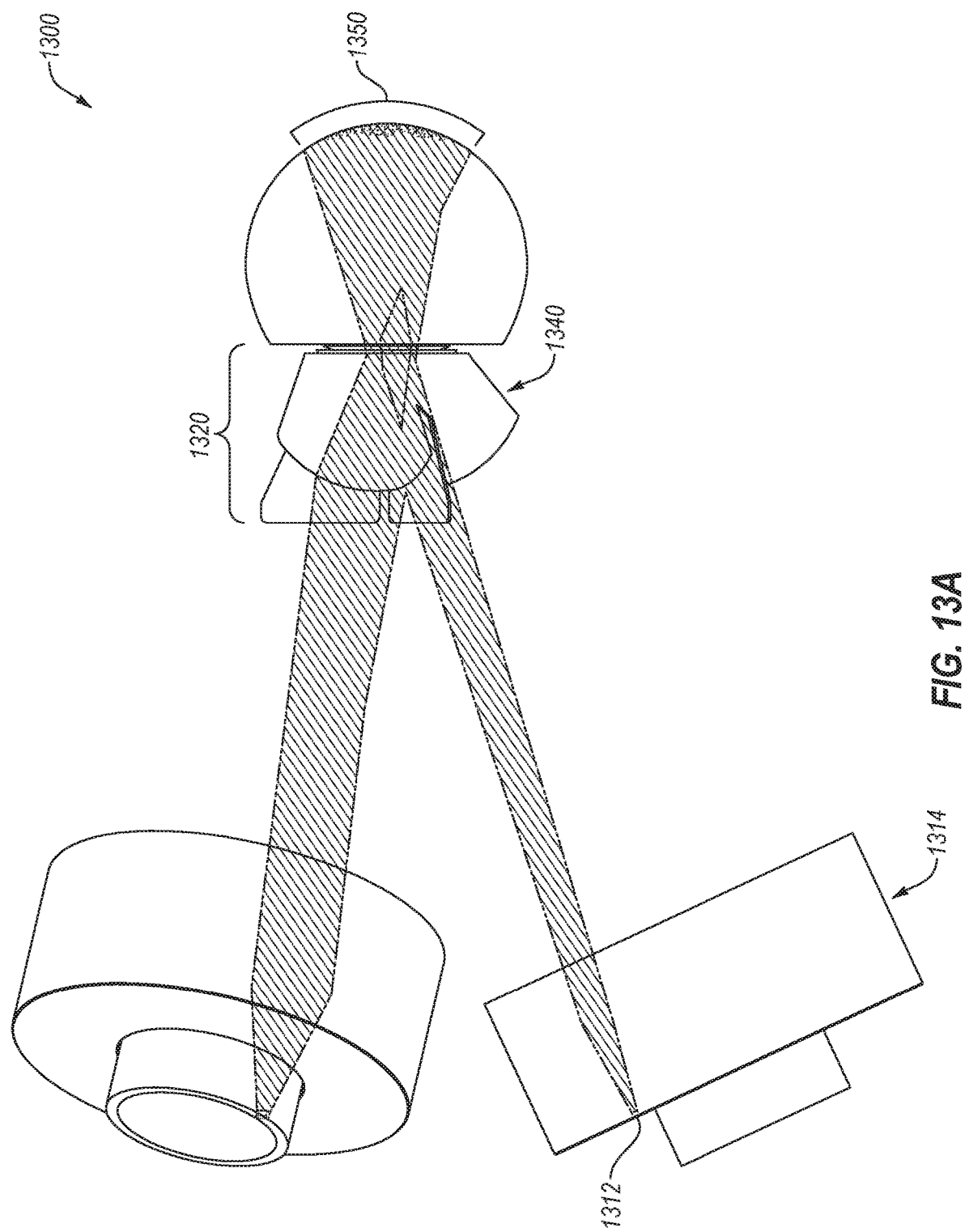
FIGS. 13A-13D illustrates an example device and components associated with guiding placement of the example device relative to the eye.
Figure 13B:
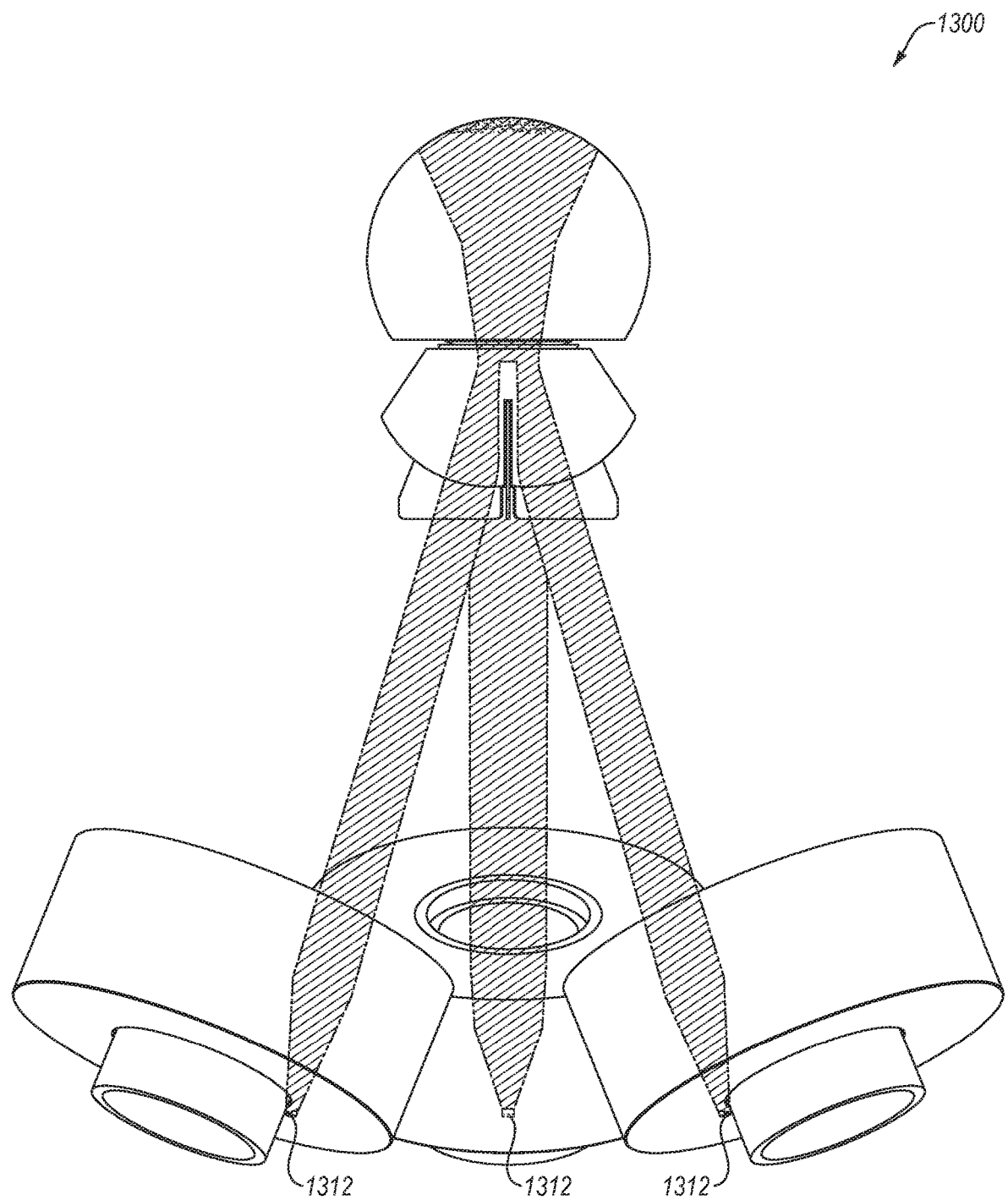
Figure 13D:
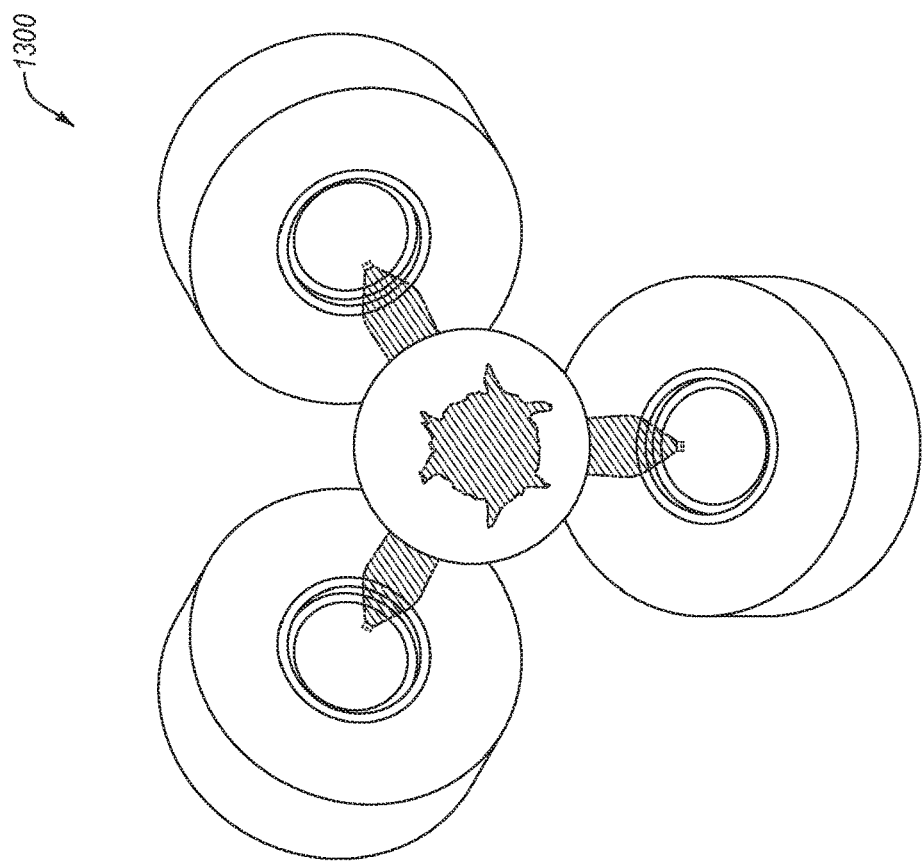
Figure 13C:
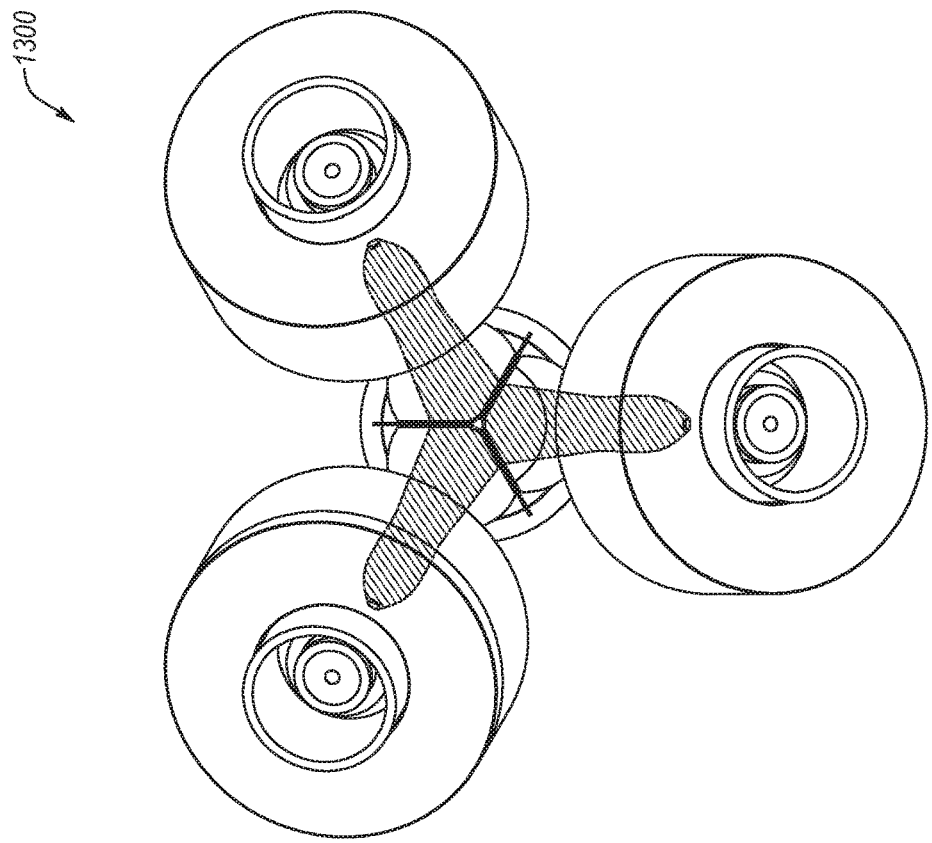

FIG. 13A illustrates a side view of the imaging system 1300, FIG. 13B illustrates a top-down view of the imaging system 1300, FIG. 13C illustrates a front view of the imaging system 1300 (e.g., from the eye looking out towards the multi-channel imaging system), and FIG. 13D illustrates a back view of the multi-channel imaging system 1300.

Figure 14:
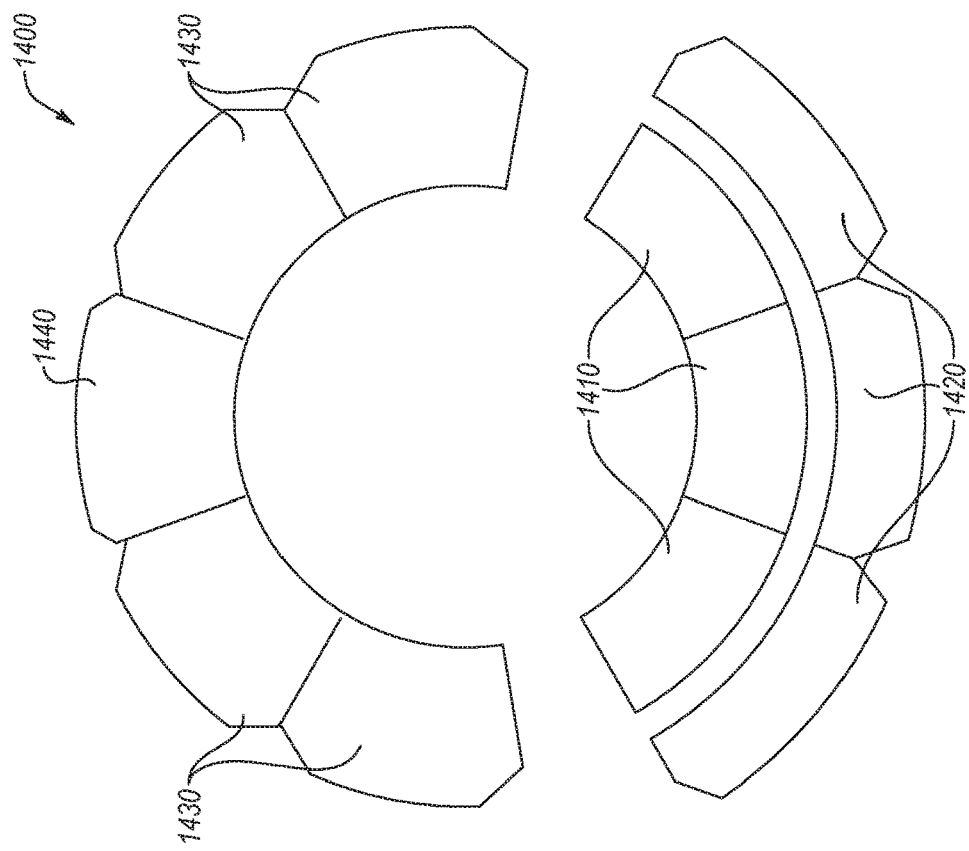
FIG. 14 illustrates an example arrangement of condensers in a device.

FIG. 14 illustrates an example arrangement 1400 of condensers. For example, the arrangement 1400 includes inner radial segment condensers 1410, outer radial segment condensers 1420, medial segment condensers 1430, and a guidance condenser 1440.

As illustrated in FIG. 14, each of the condensers 1410, 1420, 1430, and 1440 may be oriented around a central region within which the rays of the imaging channel may be directed. For each of the condensers 1410, 1420, 1430, and 1440 may be aligned symmetrically about a plane bisecting the imaging channel and the retina (as illustrated by the green arrow).

In some embodiments, the inner radial segment condensers 1410 and/or the outer radial segment condensers 1420 may be oriented along an outer edge of the imaging device (e.g., among the three imaging channels, the inner radial segment condensers 1410 and/or the outer radial segment condensers 1420 may be located on the side away from the other imaging channels). In some embodiments, the medial segment condensers 1430 and/or the guidance condensers 1440 may be oriented along an inner edge of the imaging device (e.g., among the three imaging channels, the medial segment condensers 1430 and/or the guidance condensers 1440 may be located on the side proximate to the other imaging channels). Using such an arrangement, the inner and outer radial segment illumination may project further out towards the outer portions of radial segments of the eye. In these and other embodiments, the medial segment condensers 1430 and the guidance condensers 1440 may be configured to direct the illumination towards the middle of the eye.

Figure 15:
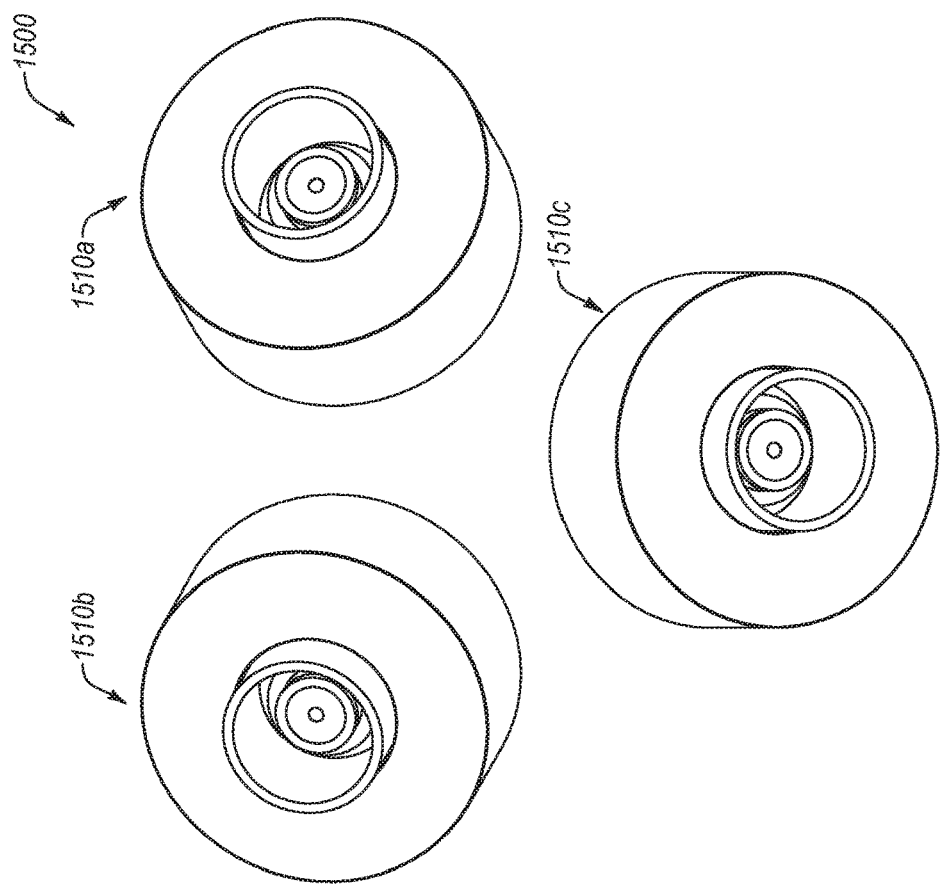
FIG. 15 illustrates an example set of imaging channels.

FIG. 15 illustrates an example set 1500 of imaging channels, including a first imaging channel 1510a, a second imaging channel 1510b, and a third imaging channel 1510c. As described above, each of the individual channels may be individually imaged and/or illuminated, including illuminating a specific portion as guided by one or more of the condensers illustrated in the present disclosure.

Figure 16:
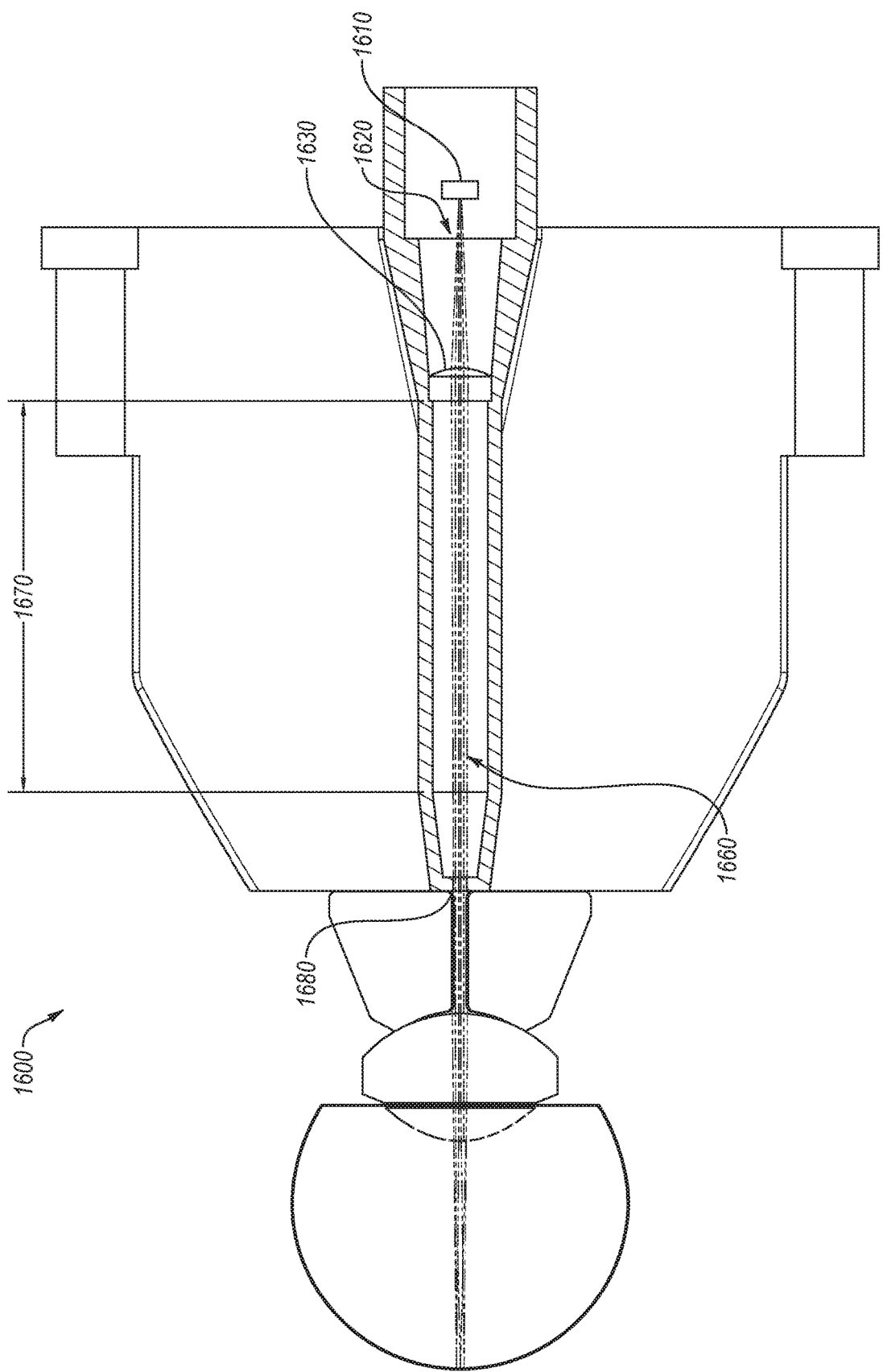
FIG. 16 illustrates an example device with a fixation system that generates fixation rays of illumination upon which the eye will focus during operation of the example device.

FIG. 16 illustrates an example imaging device 1600 including a fixation system that generates fixation rays 1660 of illumination upon which the eye will focus during operation of the imaging device 1600. As illustrated in FIG. 16, the fixation system may be positioned and oriented proximate the center of the imaging device 1600 or along a central axis of the imaging device 1600, with imaging and illumination channels positioned around the fixation system. For example, the fixation system may be on the same axis as the eye is focused, while the imaging channels are oriented around the central channel. In some embodiments, the fixation system may be located within one or more of the optical imaging systems rather than outside of the optical imaging systems.

The fixation system may include an LED 1610, an aperture 1620, and a lens 1630 to direct the fixation rays 1660 towards the retina of the eye. The LED 1610 may be any device configured to emit a beam of light. The LED 1610 may be selected to limit an amount of scatter into other lenses or portions of the imaging device 1600.

In some embodiments, the LED 1610, the aperture 1620, and the lens 1630 may be selected to provide a focused beam of light to the eye (represented by the fixation rays 1660). In these and other embodiments, the fixation rays 1660 may convene past the aperture 1620 into a beam that projects through a focusing chamber 1670. In some embodiments, the aperture(s) may create a focused pattern of fixation light, thereby creating a discrete fixation pattern for the eye to view.

The focusing chamber 1670 may be a chamber with light absorbing regions and materials within the chamber. The chamber may include an opening proximate the region where the lens 1630 and the LED 1610 cause the beams to coalesce and may include a pinhole opening 1680 on the opposite side of the focusing chamber 1670. In some embodiments, the opening near the LED 1610 may also be a pinhole opening. In these and other embodiments, by using the focusing chamber 1670, any light beams from the LED 1610 that are not narrowly directed towards the retina may be absorbed within the focusing chamber 1670. In this way, a highly focused fixation beam may be generated upon which the eye may focus during use. Because the fixation rays 1660 are focused to a narrow beam, the size of the fixation system is minimized such that most of the volume of the imaging device 1600 is available for the imaging channels. According to such an arrangement, a clear line-of-sight may exist between the LED 1610 and the retina of the eye.

In some embodiments, one or more imaging channels may share the central axis with the fixation system. For example, a medial illuminating and imaging channel for illuminating and imaging the medial portion of the posterior segment may share the central axis of the imaging device 1600. In these and other embodiments, a beam splitter may be positioned between the central axis imaging camera and the eye such that the fixation system may share the same central axis.

In some embodiments, a set of optical components (such as the aperture 1620, the lens 1630, and/or other components) may be selected, designed, and/or positioned to image the aperture 1620 onto the retina of the eye, through the clear line of sight enabled by the pinhole opening exiting the focusing chamber 1670, such that the eye may see and focus on a resolvable spot, which may be used during image capture as a fixation target for the eye, such that the ocular surfaces of the eye, such as the crystalline lens, are in a fixed position while the eye is focused on the resolvable spot, thereby reducing variation in the position and imaging properties of the eye during image capture.

In some embodiments, the imaging device may include or be communicatively coupled to a computing device. For example, the computing device may include memory and at least one processor, which are configured to perform operations as described in this disclosure, among other operations. In some embodiments, the computing device may include computer-readable instructions that are configured to be executed by the imaging device to perform operations described in this disclosure. In some embodiments, the computing device may instruct the imaging device to illuminate one or more illumination channels, such as the inner radial segment illumination, the outer radial segment illumination, etc. Additionally or alternatively, the computing device may capture and/or store images captured by the camera sensors.

Generally, the processor may include any suitable special-purpose or general-purpose computer, computing entity, or processing device including various computer hardware or software modules and may be configured to execute instructions stored on any applicable computer-readable storage media. For example, the processor may include a microprocessor, a microcontroller, a digital signal processor (DSP), an application-specific integrated circuit (ASIC), a Field-Programmable Gate Array (FPGA), or any other digital or analog circuitry configured to interpret and/or to execute program instructions and/or to process data.

It is understood that the processor may include any number of processors distributed across any number of networks or physical locations that are configured to perform individually or collectively any number of operations described herein. In some embodiments, the processor may interpret and/or execute program instructions and/or processing data stored in the memory. By interpreting and/or executing program instructions and/or process data stored in the memory, the device may perform operations, such as the operations performed by the retinal imaging device described in the present disclosure.

The memory may include computer-readable storage media or one or more computer-readable storage mediums for carrying or having computer-executable instructions or data structures stored thereon. Such computer-readable storage media may be any available media that may be accessed by a general-purpose or special-purpose computer, such as the processor. By way of example, and not limitation, such computer-readable storage media may include non-transitory computer-readable storage media including Random Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store desired program code in the form of computer-executable instructions or data structures and which may be accessed by a general-purpose or special-purpose computer. Combinations of the above may also be included within the scope of computer-readable storage media. In these and other embodiments, the term "non-transitory" as used herein should be construed to exclude only those types of transitory media that were found to fall outside the scope of patentable subject matter in the Federal Circuit decision of In re Nuijten, 500 F.3d 1346 (Fed. Cir. 2007). In some embodiments, computer-executable instructions may include, for example, instructions and data configured to cause the processor to perform a certain operation or group of operations as described in the present disclosure.

In accordance with common practice, the various features illustrated in the drawings may not be drawn to scale. The illustrations presented in the present disclosure are not meant to be actual views of any particular apparatus (e.g., device, system, etc.) or method, but are merely idealized representations that are employed to describe various embodiments of the disclosure. Accordingly, the dimensions of the various features may be arbitrarily expanded or reduced for clarity. In addition, some of the drawings may be simplified for clarity. Thus, the drawings may not depict all of the components of a given apparatus (e.g., device) or all operations of a particular method.

Terms used herein and especially in the appended claims (e.g., bodies of the appended claims) are generally intended as "open" terms (e.g., the term "including" should be interpreted as "including, but not limited to," the term "having" should be interpreted as "having at least," the term "includes" should be interpreted as "includes, but is not limited to," etc.).

Additionally, if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." or "one or more of A, B, and C, etc." is used, in general such a construction is intended to include A alone, B alone, C alone, A and B together, A and C together, B and C together, or A, B, and C together, etc. For example, the use of the term "and/or" is intended to be construed in this manner. Additionally, the term "about" or "approximately" should be interpreted to mean a value within 10% of actual value.

Further, any disjunctive word or phrase presenting two or more alternative terms, whether in the description, claims, or drawings, should be understood to contemplate the possibilities of including one of the terms, either of the terms, or both terms. For example, the phrase "A or B" should be understood to include the possibilities of "A" or "B" or "A and B."

However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations.

Additionally, the use of the terms "first," "second," "third," etc., are not necessarily used herein to connote a specific order or number of elements. Generally, the terms "first," "second," "third," etc., are used to distinguish between different elements as generic identifiers. Absence a showing that the terms "first," "second," "third," etc., connote a specific order, these terms should not be understood to connote a specific order. Furthermore, absence a showing that the terms "first," "second," "third," etc., connote a specific number of elements, these terms should not be understood to connote a specific number of elements. For example, a first widget may be described as having a first side and a second widget may be described as having a second side. The use of the term "second side" with respect to the second widget may be to distinguish such side of the second widget from the "first side" of the first widget and not to connote that the second widget has two sides.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

The following paragraphs list sample embodiments. Any of the embodiments may be combined in any order or combination. For example, an embodiment in a later paragraph may be combined with any combination of preceding and/or later paragraphs.

One embodiment of the present disclosure may include a device for illuminating a posterior segment of an eye may include multiple channels. Each of the channels may include including a first region illumination path, and a second region illumination path. The first region illumination path and the second region illumination path may be illuminated at different times such that a first region and a second region may be imaged without interference from a non-illuminated illumination path.

In combination and/or consistent with any of the embodiments described herein, a device may include a window at an end of the multiple channels proximate the eye, where the window may shared by at least two of the multiple channels.

In combination and/or consistent with any of the embodiments described herein, the window may be an interface between at least two of the multiple imaging channels and the eye.

The device of claim 1, wherein the plurality of channels includes three channels oriented between approximately five degrees and forty-five degrees off of the center axis of the eye and spaced approximately equally around the center of the eye.

In combination and/or consistent with any of the embodiments described herein, the multiple channels may converge at a single point proximate the eye, and a device may include a multi-sectioned wall disposed at the single point.

In combination and/or consistent with any of the embodiments described herein, each section of the multi-sectioned wall may be shaped and positioned to act as a baffle to prevent light from crossing between the multiple channels within the device.

In combination and/or consistent with any of the embodiments described herein, a first channel of the multiple channels may include a camera sensor approximately in line with a center line of the first channel.

In combination and/or consistent with any of the embodiments described herein, a device may further include a first illumination source for the first illumination path of the first channel and a second illumination source for the second illumination path of the first channel, where both of the first illumination source and the second illumination source may be disposed at a position offset from the center line of the first channel.

In combination and/or consistent with any of the embodiments described herein, a first channel of the multiple channels may also include a third illumination path.

In combination and/or consistent with any of the embodiments described herein, the first illumination path may illuminate an outer radial portion of posterior segment of the eye, the second illumination path may illuminate an inner radial portion of the posterior segment of the eye, and the third illumination path may illuminate an medial portion of the posterior segment of the eye.

In combination and/or consistent with any of the embodiments described herein, the outer radial portion may include approximately 50-90 degrees from the fovea, the inner radial portion may include approximately 30-60 degrees from the fovea, and the medial portion may include approximately minus 15-positive 40 degrees from the fovea.

In combination and/or consistent with any of the embodiments described herein, the first illumination path for each of the multiple channels may be illuminated simultaneously.

In combination and/or consistent with any of the embodiments described herein, the first illumination path for each of the multiple channels may be illuminated independently.

In combination and/or consistent with any of the embodiments described herein, a first channel of the multiple channels may also include a base component, where the base component may include a camera within a casing, the camera aligned with a center axis of the first channel. The base component may also include a first illumination source associated with the first illumination path and located outside of the casing, an aperture associated with the first illumination source, and an illumination condenser system to provide beam control and steering of light from the first illumination source, where the illumination condenser system may be located outside of the casing and orthogonal to the center axis of the first channel. The base component may also include a baffle to block stray illumination from the first illumination source, where the baffle may be approximately even with a top of the casing within which the camera is disposed.

In combination and/or consistent with any of the embodiments described herein, the base component may also include a prepolarizer to polarize the light from the first illumination source:

In combination and/or consistent with any of the embodiments described herein, a device may also include a cleanup polarizer positioned along an imaging pathway back to the camera such that light of a same polarization as the light exiting the prepolarizer is filtered from reaching the camera.

In combination and/or consistent with any of the embodiments described herein, the illumination condenser system may include at least one of a reflective micro-electromechanical systems (MEMS) micromirror array or a transmissive spatial light modulator.

In combination and/or consistent with any of the embodiments described herein, the first channel may also include an objective lens system at an opposite end of the first channel from the base component configured to route the light from the first illumination source into the eye.

In combination and/or consistent with any of the embodiments described herein, the objective lens system may be configured to cause the light from the first illumination source to be at its narrowest point in a cornea of the eye or between the cornea and a posterior crystalline lens of the eye.

In combination and/or consistent with any of the embodiments described herein, the base component may also include a second illumination source corresponding to the second illumination path and a third illumination source corresponding to a third illumination path.

In combination and/or consistent with any of the embodiments described herein, the first illumination path may illuminate an inner radial segment of the posterior segment of the eye and the first illumination source may be located outside of the casing and towards an outer edge of the device, the second illumination path may illuminate an outer radial segment of the posterior segment of the eye and the second illumination source may be located outside of the casing and towards the outer edge of the device, and the third illumination path may illuminate a medial segment of the posterior segment of the eye and the third illumination source may be located outside of the casing and towards an inside region of the device.

In combination and/or consistent with any of the embodiments described herein, each of the multiple channels may include a guidance illumination source used to align the device to the eye, where the guidance illumination source of the first channel may be located outside the casing and towards the inside region of the device, and each of the guidance illumination sources for each of the multiple channels may be configured to illuminate such that light from the guidance illumination sources reflects off of the eye as the device is brought close to the eye.

In combination and/or consistent with any of the embodiments described herein, a device may also include a fixation system, where the fixation system may include a fixation light source located within a central region of the device and aligned with a center line of the device, and a focusing chamber through which light from the fixation light source passes, where the focusing chamber may include a pinhole at an end of the focusing chamber opposite the fixation light source.

What is claimed is:

1. A device for illuminating a posterior segment of an eye, including:
    a plurality of channels, each of the plurality of channels including:
        a first region illumination path; and
        a second region illumination path; and
        wherein the first region illumination path and the second region illumination path are illuminated at different times such that a first region and a second region may be imaged without interference from a non-illuminated illumination path, and
    wherein the plurality of channels converge at a single point proximate the eye, the device further comprising a multi-sectioned wall disposed at the single point.

2. The device of claim 1, further comprising a window at an end of the plurality of channels proximate the eye, the window shared by at least two of the plurality of channels.

3. The device of claim 2, wherein the window is an interface between the at least two of the plurality of channels and the eye.

4. The device of claim 1, wherein the plurality of channels includes three channels oriented between approximately five degrees and forty-five degrees off of a central axis of the device and spaced approximately equally around the central axis of the device, the central axis of the device generally aligned with a central axis of the eye.

5. The device of claim 1, wherein each section of the multi-sectioned wall is shaped and positioned to act as a baffle to prevent light from crossing between the plurality of channels within the device.

6. The device of claim 1, wherein a first channel of the plurality of channels includes a camera sensor approximately in line with a center line of the first channel.

7. The device of claim 6, further comprising a first illumination source for the first illumination path of the first channel and a second illumination source for the second illumination path of the first channel, both of the first illumination source and the second illumination source disposed at a position offset from the center line of the first channel.

8. The device of claim 1, wherein a first channel of the plurality of channels further includes a third illumination path.

9. The device of claim 8, wherein the first illumination path illuminates an outer radial portion of the posterior segment of the eye, the second illumination path illuminates an inner radial portion of the posterior segment of the eye, and the third illumination path illuminates a medial portion of the posterior segment of the eye.

10. The device of claim 9, wherein the outer radial portion includes approximately 50-90 degrees relative to an axis extending from a fovea of the eye, the inner radial portion includes approximately 30-60 degrees relative to the axis extending from the fovea, and the medial portion includes approximately minus 15-positive 40 degrees relative to the axis extending from the fovea.

11. The device of claim 9, wherein the first illumination path for each of the plurality of channels are illuminated simultaneously.

12. The device of claim 9, wherein the first illumination path for each of the plurality of channels are illuminated independently.

13. A device for illuminating a posterior segment of an eye, including:
    a plurality of channels, each of the plurality of channels including:
        a first region illumination path; and
        a second region illumination path,
        wherein the first region illumination path and the second region illumination path are illuminated at different times such that a first region and a second region may be imaged without interference from a non-illuminated illumination path, wherein a first channel of the plurality of channels further includes a base component, the base component comprising:

a camera within a casing, the camera aligned with a center axis of the first channel;

a first illumination source associated with the first illumination path and located outside of the casing;

an aperture associated with the first illumination source;

an illumination condenser system to provide beam control and steering of light from the first illumination source, the illumination condenser system located outside of the casing and orthogonal to the center axis of the first channel; and a baffle to block stray illumination from the first illumination source, the baffle approximately even with a top of the casing within which the camera is disposed.

14. The device of claim 13, wherein the base component further comprises a prepolarizer to polarize the light from the first illumination source.

15. The device of claim 14, further comprising a cleanup polarizer positioned along an imaging pathway back to the camera such that light of a same polarization as the light exiting the prepolarizer is filtered from reaching the camera.

16. The device of claim 13, wherein the illumination condenser system includes at least one of a reflective microelectromechanical systems (MEMS) micromirror array or a transmissive spatial light modulator.

17. The device of claim 13, wherein the first channel further comprises an objective lens system at an opposite end of the first channel from the base component configured to route the light from the first illumination source into the eye.

18. The device of claim 17, wherein the objective lens system is configured to cause the light from the first illumination source to be at its narrowest point in a cornea of the eye or between the cornea and a posterior crystalline lens of the eye.

19. The device of claim 13, wherein the base component further comprises a second illumination source corresponding to the second illumination path and a third illumination source corresponding to a third illumination path.

20. The device of claim 19, wherein:

the first illuminati on path illuminates an inner radial segment of the posterior segment of the eye and the first illumination source is located outside of the casing and towards an outer edge of the device;

the second illumination path illuminates an outer radial segment of the posterior segment of the eye and the second illumination source is located outside of the casing and towards the outer edge of the device; and the third illumination path illuminates a medial segment of the posterior segment of the eye and the third illumination source is located outside of the casing and towards an inside region of the device.

21. The device of claim 20, wherein:

each of the plurality of channels includes a guidance illumination source used to align the device to the eye;

the guidance illumination source of the first channel is located outside the casing and towards the inside region of the device; and wherein each of the guidance illumination sources for each of the plurality of channels are configured to illuminate such that light from the guidance illumination sources reflects off of the eye as the device is brought close to the eye.

22. The device of claim 1, further comprising a fixation system, the fixation system including:

a fixation light source located within a central region of the device and aligned with a center line of the device; and a focusing chamber through which light from the fixation light source passes, the focusing chamber including a pinhole at an end of the focusing chamber opposite the fixation light source.

23. A device for illuminating a posterior segment of an eye, including:

a plurality of channels, each of the plurality of channels including:

a first region illumination path; and a second region illumination path, wherein a first channel of the plurality of channels further includes a third illumination path, and wherein the first region illumination path and the second region illumination path are illuminated at different times such that a first region and a second region may be imaged without interference from a non-illuminated illumination path, wherein the first illumination path illuminates only an outer radial portion of the posterior segment of the eye, the second illumination path illuminates only an inner radial portion of the posterior segment of the eye, and the third illumination path illuminates only a medial portion of the posterior segment of the eye.

* * * * *